United States Patent
Sakagawa

(10) Patent No.: US 8,876,291 B2
(45) Date of Patent: Nov. 4, 2014

(54) CONTROL APPARATUS, OPHTHALMOLOGIC APPARATUS, SYSTEM, CONTROL METHOD, AND PROGRAM

(75) Inventor: Yukio Sakagawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/426,441

(22) Filed: Mar. 21, 2012

(65) Prior Publication Data

US 2012/0249952 A1 Oct. 4, 2012

(30) Foreign Application Priority Data

Mar. 31, 2011 (JP) ................................. 2011-079365

(51) Int. Cl.
*A61B 3/14* (2006.01)
*A61B 3/00* (2006.01)

(52) U.S. Cl.
CPC .................................... *A61B 3/0075* (2013.01)
USPC ............................ 351/206; 351/205; 351/210

(58) Field of Classification Search
USPC ......................................... 351/206, 205, 210
See application file for complete search history.

(56) References Cited

U.S. PATENT DOCUMENTS

| 5,526,072 A | 6/1996 | El Hage |
| 5,568,208 A | 10/1996 | Van de Velde |
| 2003/0120266 A1* | 6/2003 | Fujieda ............................. 606/5 |
| 2005/0105049 A1 | 5/2005 | Maeda |
| 2009/0149742 A1* | 6/2009 | Kato et al. .................... 600/425 |
| 2009/0323023 A1 | 12/2009 | Kogawa |
| 2010/0110172 A1 | 5/2010 | Satake |
| 2010/0128960 A1 | 5/2010 | Yumikake |

FOREIGN PATENT DOCUMENTS

| CN | 001618394 A | 5/2005 |
| EP | 1316287 A2 | 6/2003 |
| JP | 2005-143903 A | 6/2005 |
| WO | 2006/106977 A1 | 10/2006 |

* cited by examiner

*Primary Examiner* — Ricky Mack
*Assistant Examiner* — Mustak Choudhury
(74) *Attorney, Agent, or Firm* — Canon U.S.A., Inc. IP Division

(57) ABSTRACT

A control apparatus includes a display control unit configured to cause a display unit to display an image of an anterior segment of a subject's eye captured by an imaging unit, and a control unit configured to output, based on an operation signal output from a mouse according to an operation on the mouse when an index indicating an arbitrary position on the display unit is located on the image of the anterior segment, a control signal indicating a change amount in an optical axis direction of the imaging unit of a focal position of the image of the anterior segment relative to the imaging unit.

26 Claims, 16 Drawing Sheets

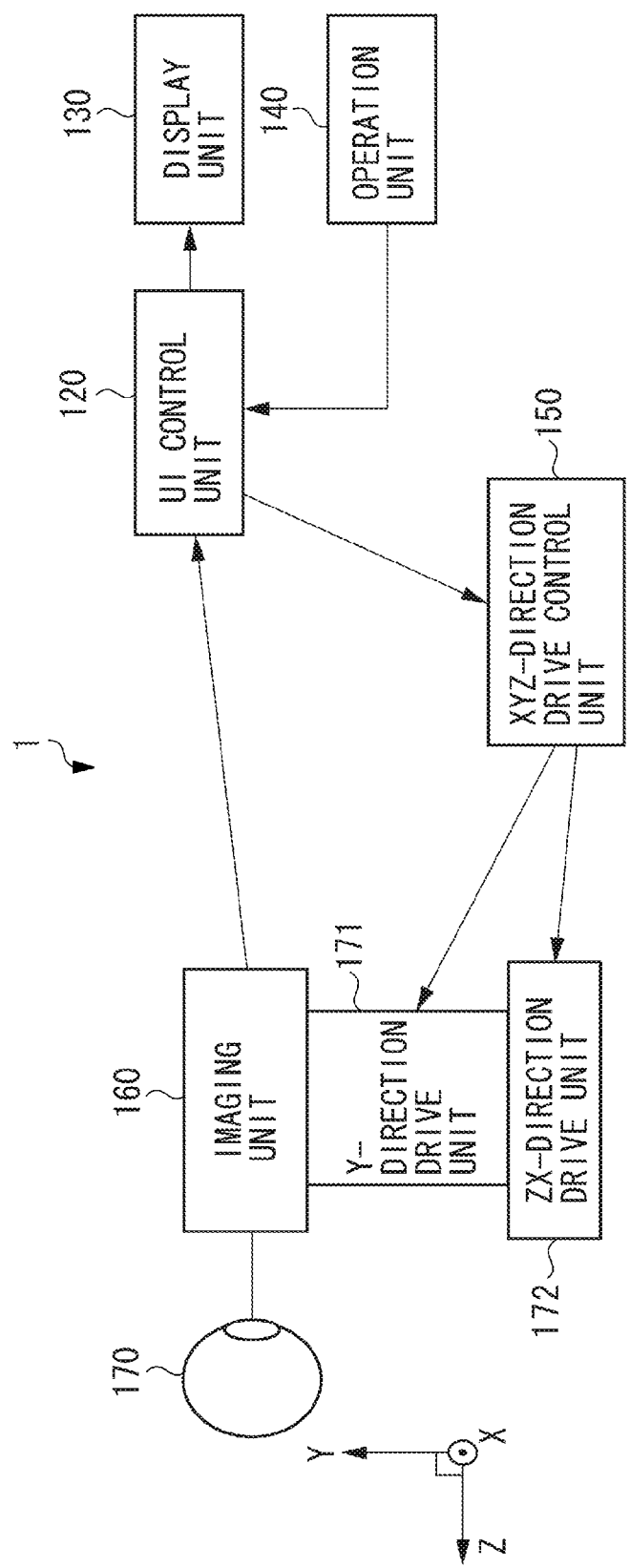

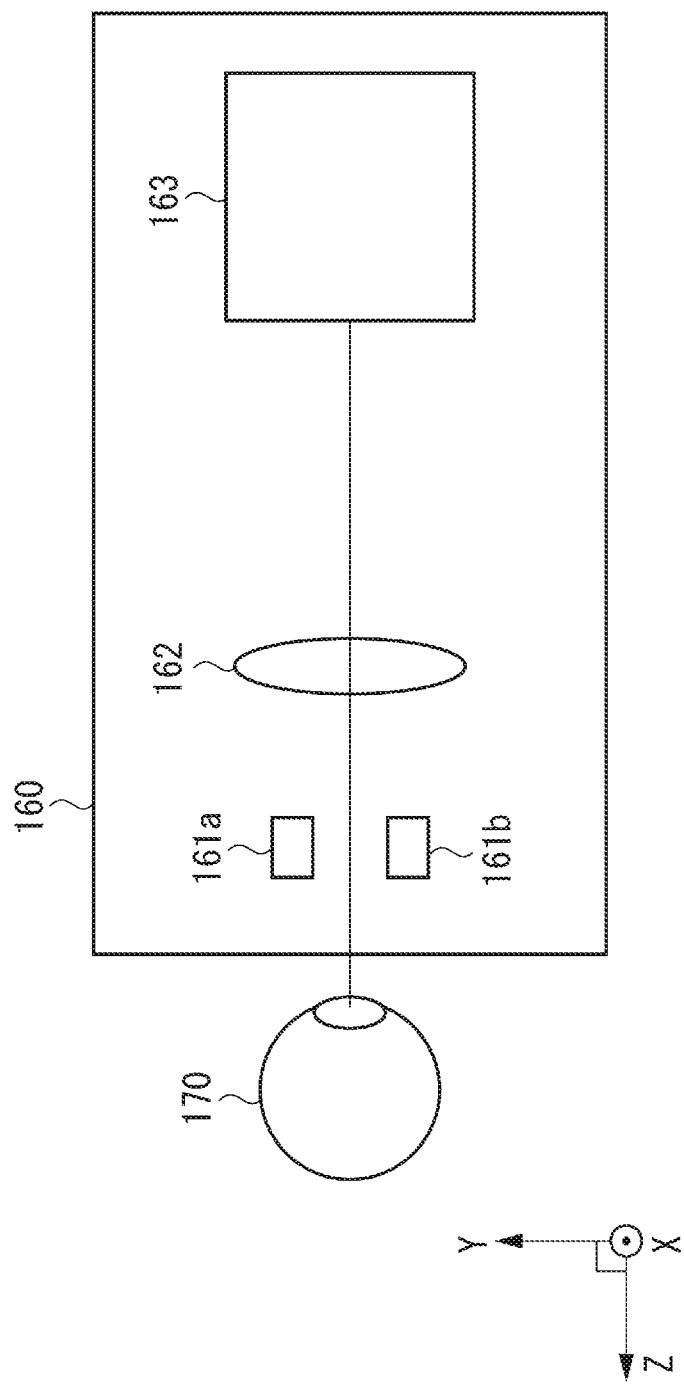

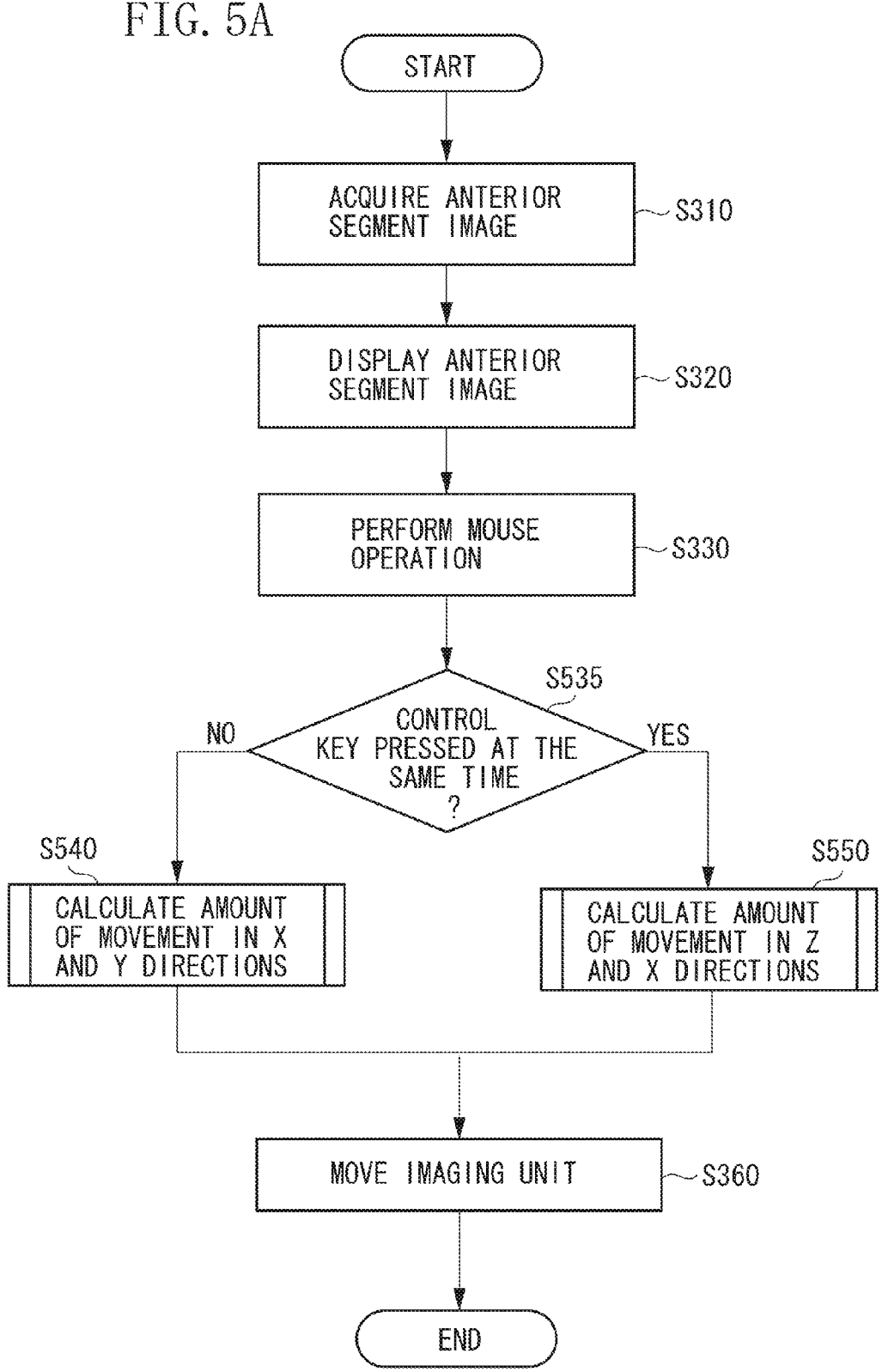

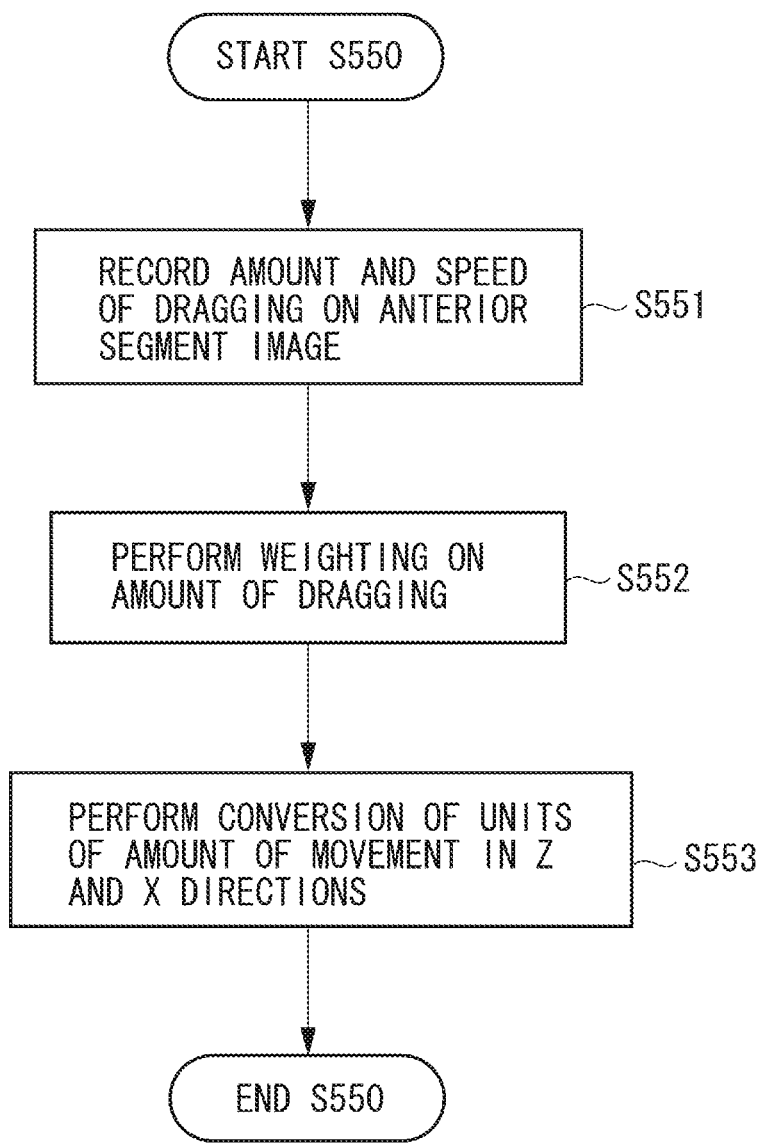

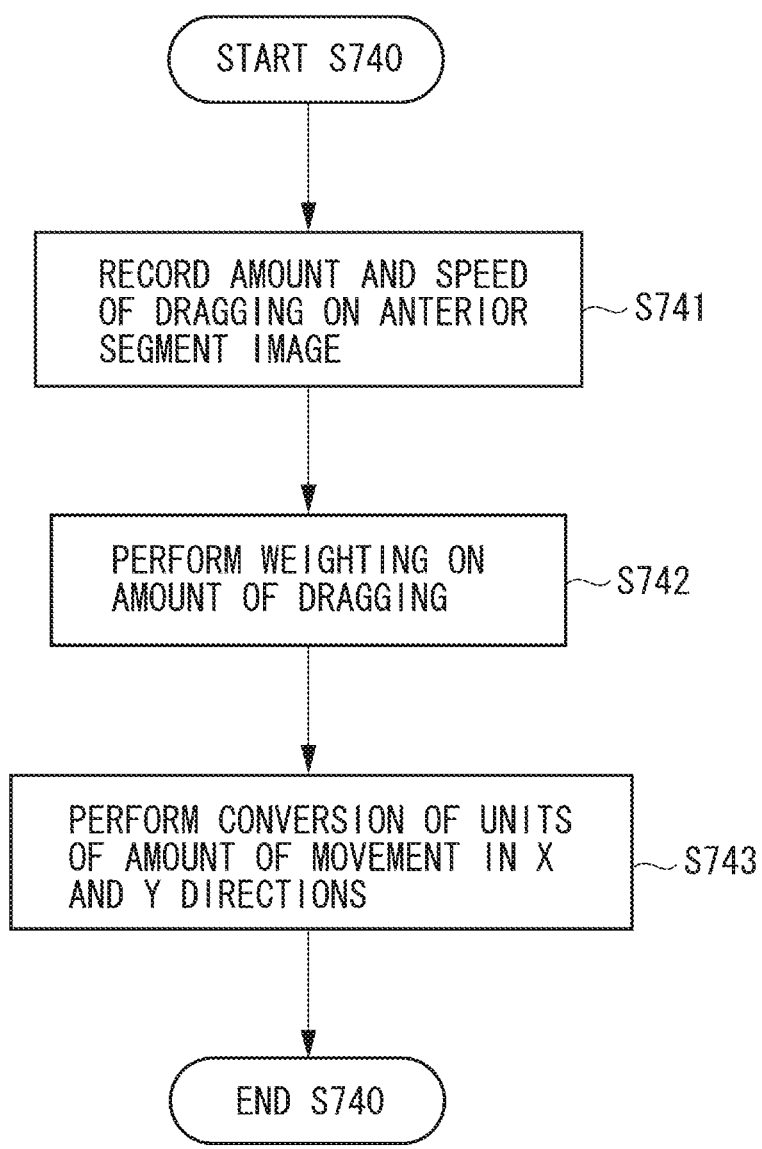

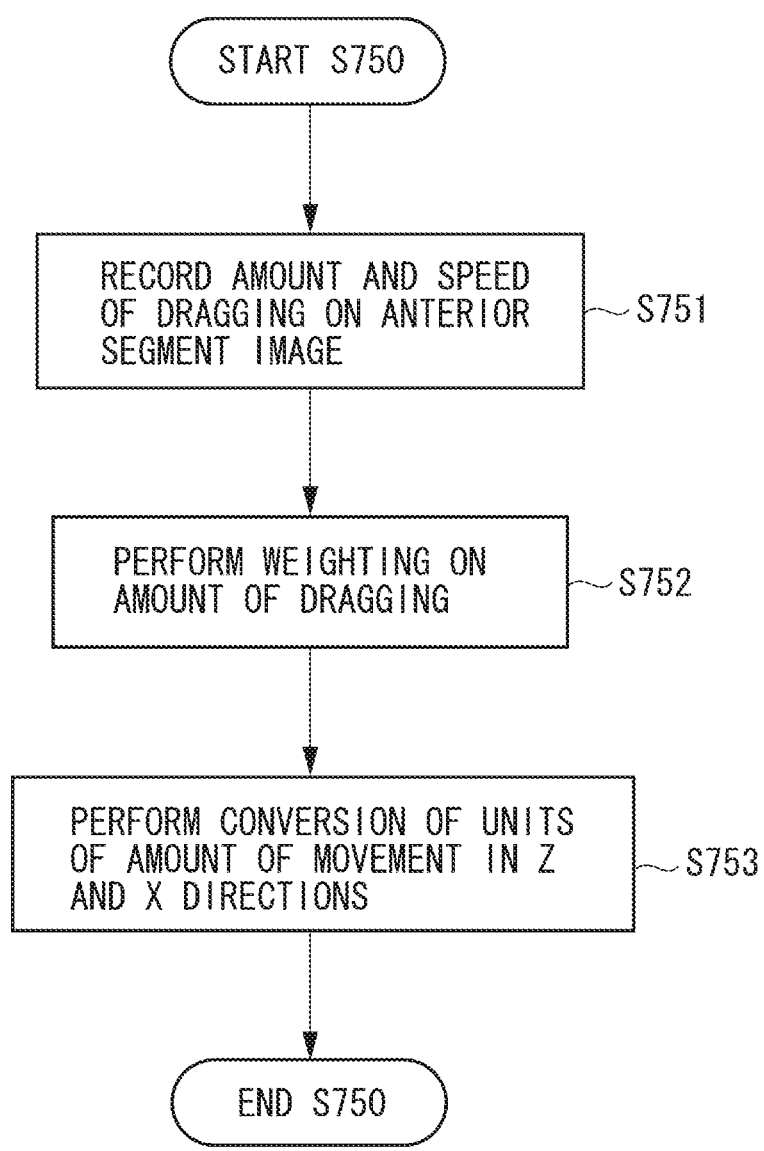

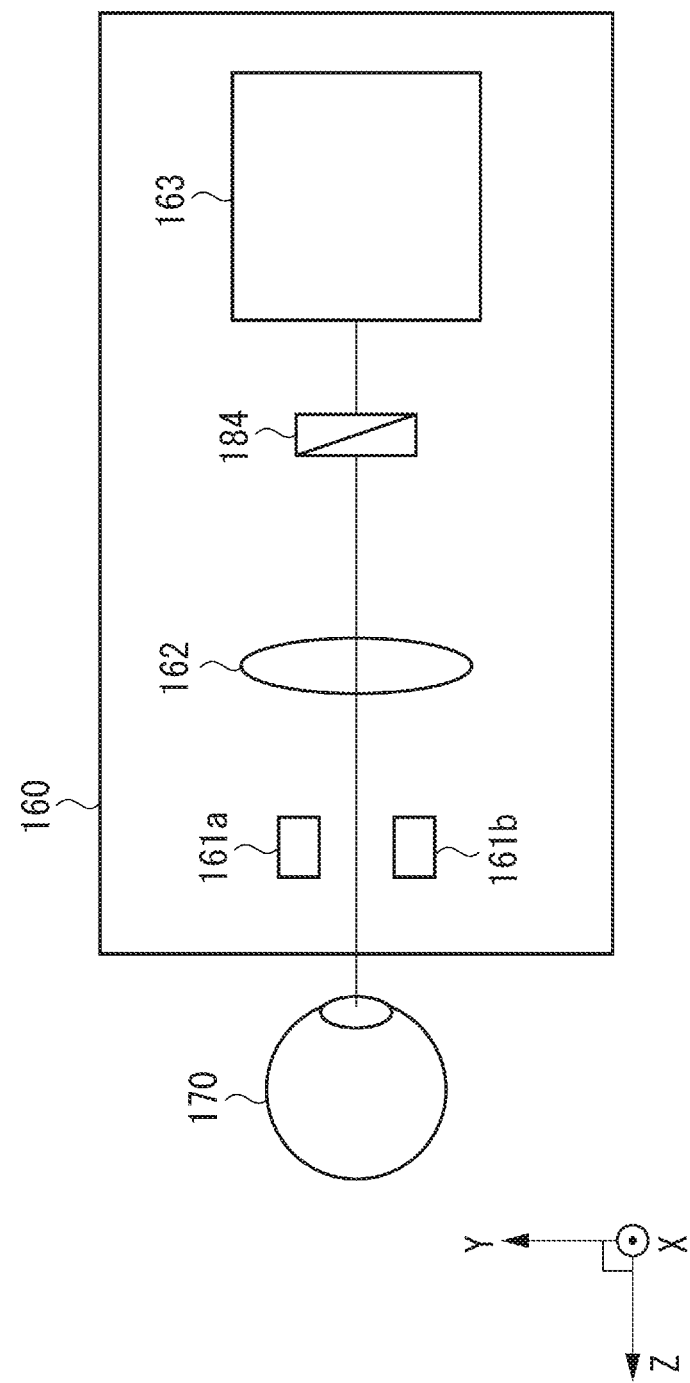

CONTROL APPARATUS, OPHTHALMOLOGIC APPARATUS, SYSTEM, CONTROL METHOD, AND PROGRAM

BACKGROUND OF THE INVENTION

1. Field of the Invention

The present invention relates to a control apparatus, an ophthalmologic apparatus, a system, a control method, and a program.

2. Description of the Related Art

There is a technique which moves in three-dimensional directions a measurement unit including an image sensor that captures an image of the anterior segment of a subject's eye (an eye to be examined). The measurement unit is thus aligned with the anterior segment of the subject's eye.

Further, Japanese Patent Application Laid-Open No. 2005-143903 discusses a technique in which an operator clicks using a mouse on one point on an image of the anterior segment displayed on a display device. The measurement unit is then aligned in a planar direction perpendicular to a depth direction of the subject's eye so that the clicked point is positioned at the center of a display area of the anterior segment on the display device.

However, the measurement unit cannot be aligned in the depth direction of the subject's eye by an operation performed by the operator on the anterior segment image displayed on the display device. In such a case, the operator manipulates the measurement unit using a joystick to align the measurement unit in the depth direction. As a result, if the measurement unit is to be aligned in the three-dimensional direction including the depth direction of the subject's eye, it becomes necessary for the operator to perform both an operation on the anterior segment image and an operation on the joystick. It is thus burdensome and time-consuming to perform alignment.

SUMMARY OF THE INVENTION

The present invention is directed to a control apparatus capable of easily performing alignment in the three-dimensional direction including the depth direction of a subject's eye.

According to an aspect of the present invention, a control apparatus includes a display control unit configured to cause a display unit to display an image of an anterior segment of a subject's eye captured by an imaging unit, and a control unit configured to output, based on an operation signal output from a mouse according to an operation on the mouse when an index indicating an arbitrary position on the display unit is located on the image of the anterior segment, a control signal indicating a change amount in an optical axis direction of the imaging unit of a focal position of the image of the anterior segment relative to the imaging unit.

According to another aspect of the present invention, an ophthalmologic apparatus includes an imaging unit configured to capture an image of an anterior segment of a subject's eye, and a changing unit configured to change a focal position of the image of the anterior segment relative to the imaging unit in an optical axis direction of the imaging unit based on a control signal output from a control unit according to an operation on a mouse when an index indicating an arbitrary position on a display unit is located on the image of the anterior segment displayed on the display unit.

According to yet another aspect of the present invention, a system includes an imaging unit configured to capture an image of an anterior segment of a subject's eye, a display unit configured to display the image of the anterior segment, a control unit configured to output, based on an operation signal output from a mouse according to an operation on the mouse when an index indicating an arbitrary position on the display unit is located on the image of the anterior segment, a control signal indicating a change amount in an optical axis direction of the imaging unit of a focal position of the image of the anterior segment relative to the imaging unit, and a changing unit configured to change the focal position in the optical axis direction of the imaging unit based on the control signal.

According to yet another aspect of the present invention, a control method includes causing a display unit to display an image of an anterior segment of a subject's eye captured by an imaging unit, and outputting, based on an operation signal output from a mouse according to an operation on the mouse when an index indicating an arbitrary position on the display unit is located on the image of the anterior segment, a control signal indicating a change amount in an optical axis direction of the imaging unit of a focal position of the anterior segment relative to the imaging unit.

According to yet another aspect of the present invention, a computer-readable storage medium stores a program that causes a computer to execute the above-described control method.

According to an exemplary embodiment of the present invention, alignment in the three-dimensional direction including the depth direction of a subject's eye can be easily performed.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 1 is a block diagram illustrating a functional configuration of a system according to a first exemplary embodiment of the present invention.

FIG. 2 illustrates a configuration of an imaging unit according to the first exemplary embodiment.

FIGS. 5A, 5B, and 5C are flowcharts illustrating a system operation according to a second exemplary embodiment of the present invention.

FIGS. 7A, 7B, and 7C are flowcharts illustrating a system operation according to a third exemplary embodiment of the present invention.

FIG. 9 illustrates a configuration of an imaging unit according to a fourth exemplary embodiment of the present invention.

DESCRIPTION OF THE EMBODIMENTS

Figure 3A:
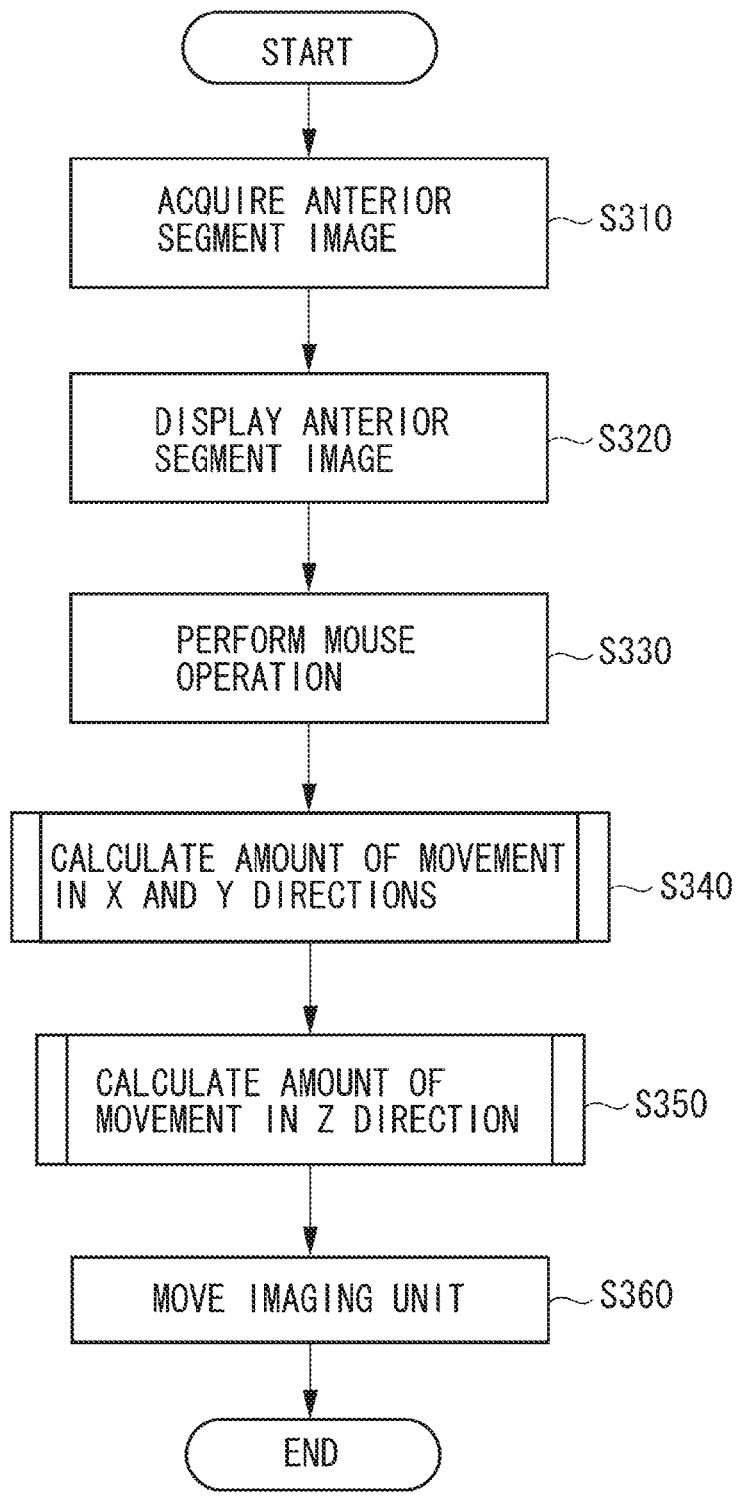
FIGS. 3A, 3B, and 3C are flowcharts illustrating a system operation according to the first exemplary embodiment.

Various exemplary embodiments, features, and aspects of the invention will be described in detail below with reference to the drawings.

FIG. 1 illustrates a system 1 according to a first exemplary embodiment of the present invention. Referring to FIG. 1, the system 1 includes a user interface (UI) control unit 120, a display unit 130, an operation unit 140, an XYZ-direction drive control unit 150, an imaging unit 160, a Y-direction drive unit 171, and a ZX-direction drive unit 172. According to the present exemplary embodiment, the imaging unit 160, the Y-direction drive unit 171, and the ZX-direction drive unit 172 configure an example of an ophthalmologic apparatus. Further, the UI control unit 120 and the XYZ-direction drive control unit 150 configure an example of a control apparatus.

According to the present exemplary embodiment, the depth direction of the drawing sheet surface indicates X direction, a horizontal direction of the drawing sheet surface indicates Z direction, and a vertical direction of the drawing sheet surface indicates Y direction. In other words, the optical axis direction of the imaging unit 160 indicates the Z direction, the vertical direction of the plane perpendicular to the optical axis of the imaging unit 160 indicates the Y direction, and the horizontal direction of the plane perpendicular to the optical axis of the imaging unit 160 indicates the X direction.

The imaging unit 160 captures an image of a subject's eye 170. More specifically, the imaging unit 160 captures an image of the anterior segment (part) of the subject's eye 170. The imaging unit 160 thus functions as an example of imaging means configured to capture an image of an anterior segment of a subject's eye.

FIG. 2 illustrates an example of the configuration of the imaging unit 160. Referring to FIG. 2, the imaging unit 160 includes anterior segment-illumination light emitting diodes (LED) 161a and 161b, an objective lens 162, and an anterior segment camera 163. The anterior segment-illumination LEDs 161a and 161b illuminate the anterior segment of the subject's eye 170. The objective lens 162 forms the image of the anterior segment on the anterior segment camera 163. The anterior segment camera 163 captures the image of the anterior segment of the subject's eye formed on a light-receiving surface.

The Y-direction drive unit 171 moves the imaging unit 160 in the Y direction (i.e., a vertical direction of the drawing sheet surface), based on the signal output from the XYZ-direction drive control unit 150. In other words, the Y-direction drive unit 171 moves the imaging unit 160 in the planar direction perpendicular to the optical axis of the imaging unit 160. The Y-direction drive unit 171 thus changes a positional relation between the subject's eye 170 and the imaging unit 160 in the planar direction perpendicular to the optical axis of the imaging unit 160. A mechanism used for moving the imaging unit 160 in the Y direction may be realized using various known means.

The ZX-direction drive unit 172 moves the imaging unit 160 separately in the Z direction and in the X direction, based on the signal output from the XYZ-direction drive control unit 150. The ZX-direction drive unit 172 includes an X-direction drive unit and a Z-direction drive unit (not illustrated) for moving the imaging unit 160 separately in the Z direction and in the X direction. The X-direction drive unit moves the imaging unit 160 in the planar direction perpendicular to the optical axis of the imaging unit 160. The X-direction drive unit thus changes the positional relation between the subject's eye 170 and the imaging unit 160 in the planar direction perpendicular to the optical axis of the imaging unit 160. The Z-direction drive unit moves the imaging unit 160 in the optical axis direction of the imaging unit 160. The Z-direction drive unit thus changes with respect to the imaging unit 160 (i.e., the anterior segment camera 163) the focal position of the anterior segment image of the subject's eye 170 in the optical axis direction of the imaging unit 160. The mechanism used for moving the imaging unit 160 in the X direction and the Z direction may be realized using various known means.

The ZX-direction drive unit 172 functions as an example of changing means configured to change with respect to the imaging unit the focal position of the anterior segment image in the optical axis direction of the imaging unit. The changing unit changes the focal position based on the control signal output from the control unit according to an operation on the operation unit when the index indicating an arbitrary position on the display unit is located on the image of the anterior segment displayed on the display unit. Further, the Y-direction drive unit 171 and the ZX-direction drive unit 172 functions as an example of changing means configured to change the positional relation between the subject's eye and the imaging unit in the planar direction perpendicular to the optical axis of the imaging unit.

The display unit 130 displays the image according to control performed by the UI control unit 120. For example, the display unit 130 displays the anterior segment image and the index. The display unit 130 thus functions as an example of display means configured to display the anterior segment image.

The operation unit 140 outputs to the UI control unit 120 an operation signal indicating an operation by an operator (not illustrated), according to the operation by the operator. Devices such as a mouse (a pointing device arranged to detect two-dimensional motion relative to its supporting surface), a keyboard, and a touch panel may be employed as the operation unit 140. For example, it is assumed that the operation unit 140 is a mouse having a button and a wheel. The operation unit 140 then receives a temporary pressing operation (i.e., clicking operation) of the button, and outputs to the UI control unit 120 the operation signal indicating that the operation unit 140 has been clicked. Further, if the wheel of the operation unit 140, e.g., the mouse, has been rotated, the operation unit 140 outputs to the UI control unit 120 the operation signal indicating an amount of rotation and a rotational direction of the wheel. Furthermore, if the operation unit 140, e.g., the mouse, has been moved, the operation unit 140 outputs to the UI control unit 120 the operation signal indicating movement of the operation unit 140.

The operation unit 140 may be configured by a single device such as a mouse or a keyboard, or may be configured by two or more devices. For example, the operation unit 140 may be configured of the mouse and the keyboard. According to the present exemplary embodiment, the operation unit 140 functions as an example of operation means.

The UI control unit 120 causes the display unit 130 to display various images based on the signals output from the imaging unit 160 and the operation unit 140. The UI control unit 120 may be realized by a processing unit such as a central processing unit (CPU) executing a program stored in a memory (not illustrated).

For example, the UI control unit 120 causes the display unit 130 to display the anterior segment image acquired by the imaging unit 160. In other words, the UI control unit 120 functions as an example of display control means configured to cause the display unit to display an image of the anterior segment of the subject's eye captured by the imaging unit.

Further, the UI control unit 120 causes the display unit 130 to display the index which moves along with an instruction from the operation unit 140 and points to an arbitrary position on the display unit 130. An arrow-type cursor may be used as the index. However, this is not a limitation, and the index may be in any form as long as it can point to an arbitrary position on the display unit 130.

Furthermore, the UI control unit 120 is capable of recognizing coordinates on the display unit 130 and an area on the display unit 130 where the index is located, based on the operation signal input from the operation unit 140. Moreover, the UI control unit 120 is capable of recognizing the coordinates of the area on the display unit 130 in which the anterior segment image is displayed. As a result, if the operation unit 140 is a mouse, the UI control unit 120 is capable of recognizing, based on the operation signal indicating movement of the mouse, the position on the display unit 130 of the index which moves according to the movement of the mouse. Further, the UI control unit 120 is capable of recognizing whether the index moving according to the operation of the operation unit 140 is positioned in the area of the display unit 130 on which the anterior image is displayed.

Furthermore, the UI control unit 120 calculates, if the index is positioned on the anterior segment image, an amount of movement of the imaging unit 160 according to the operation signal input from the operation unit 140. The UI control unit 120 may calculate the amount of movement in units of pixels, and the XYZ-direction driving control unit 150 to be described below changes the units of the amount of movement to centimeters and millimeters. More specifically, if the operation unit 140 is a mouse, and the index is positioned on the anterior segment image so that the operator clicks on the anterior segment image, the UI control unit 120 receives the operation signal corresponding to the clicking operation. The UI control unit 120 then determines as the amount of movement of the imaging unit 160 the distance between the coordinates of the index when the operator has clicked the mouse and a predetermined position of the area where the anterior segment image is displayed on the display unit 130. The units of the distance may be pixels.

Further, if the wheel of the operation unit 140, e.g., the mouse, is rotated, the UI control unit 120 receives the operation signals indicating the amount of rotation of the wheel and the rotational direction, output from the operation unit 140 as a result of rotating the wheel. The UI control unit 120 may record on a memory (not illustrated) the number of pulses and the rotational direction output from the operation unit 140 every time the wheel is rotated.

If a keyboard is to be employed as the operation unit 140, it may be assumed that the clicking operation corresponds to pressing of an enter key, and rotation of the wheel corresponds to pressing of upward and downward direction keys. Other keys on the keyboard may be used for moving the index, or the mouse may be used for moving the index.

The UI control unit 120 performs with respect to the anterior segment image, contrast adjustment, window wing adjustment, or processing such as noise filtering.

The XYZ-direction drive control unit 150 controls, based on the operation by the operator on the anterior segment observation image, the Y-direction drive unit 171 and the ZX-direction drive unit 172. More specifically, the XYZ-direction drive control unit 150 uses the amount of movement calculated by the UI control unit 120 and generates the control signals indicating the amount of movement of the imaging unit 160 in the X direction, the Y direction, and the Z direction, respectively. The XYZ-direction drive control unit 150 may be realized by the processing unit such as the CPU executing the program stored in the memory (not illustrated).

Further, the XYZ-direction drive control unit 150 transmits to the Y-direction drive unit 171 the control signal indicating the amount of movement of the imaging unit 160 in the Y-direction. The XYZ-direction drive control unit 150 thus causes the Y-direction drive unit 171 to move the imaging unit 160 in the Y direction. Furthermore, the XYZ-direction drive control unit 150 transmits to the ZX-direction drive unit 172 the control signal indicating the amount of movement of the imaging unit 160 in the X direction and the Z direction. According to the present exemplary embodiment, the amount of movement of the imaging unit 160 in the Z direction corresponds to the amount of movement in the optical axis direction of the imaging unit 160 of the focal position of the anterior segment image of the subject's eye 170, with respect to the imaging unit 160.

More specifically, the XYZ-direction drive control unit 150 transmits to the X-direction drive unit included in the ZX-direction drive unit 172 the control signal indicating the amount of movement of the imaging unit 160 in the X direction. Further, the XYZ-direction drive control unit 150 transmits to the Z-direction drive unit included in the ZX-direction drive unit 172 the control signal indicating the amount of movement of the imaging unit 160 in the Z direction. As a result of transmitting the control signals with respect to the X direction and the Z direction, the XYZ-direction drive control unit 150 causes the ZX-direction drive unit 172 to move the imaging unit 160 in the Z direction and the X direction. The XYZ-direction drive control unit 150 moves the imaging unit 160 in the Z direction, and thus changes the position in the optical axis direction of the imaging unit 160 (i.e., the anterior segment camera 163) of a focal position of the anterior segment image of the subject's eye 170 with respect to the imaging unit 160.

As a result, the control signal indicating the amount of movement of the imaging unit 160 in the Z direction indicates the change amount in the optical axis direction of the imaging unit 160 of a focal position of the anterior segment image of the subject's eye with respect to the imaging unit 160. In other words, the XYZ-direction drive control unit 150 functions as an example of control means configured to output the control signal indicating the change amount in the optical axis direction of the imaging unit of the focal position of the anterior segment image with respect to the imaging unit. The control unit outputs the control signal based on the operation signal output from the operation unit according to the operation on the operation unit when the index indicating an arbitrary position on the display unit is located on the anterior segment image.

Further, the control signal indicating the amounts of movement of the imaging unit 160 in the X direction and the Y direction are signals indicating the change amount of the positional relation between the subject's eye 170 in the planar direction perpendicular to the optical axis of the imaging unit 160 and the imaging unit 160. In other words, the control signal indicating the amounts of movement of the imaging unit 160 in the X direction and the Y direction is an example of a control signal indicating the change amount of the position relation between the subject's eye in the planar direction perpendicular to the optical axis of the imaging unit and the imaging unit.

According to the present exemplary embodiment, the XYZ-direction drive control unit 150 converts the amount of movement of the imaging unit 160 calculated by the UI control unit 120 in units of pixels to the amount of movement in units of centimeters and millimeters. More specifically, a size corresponding to one pixel in the anterior segment is stored in a memory (not illustrated). The XYZ-direction drive control unit 150 then uses the above-described correspondence relation to convert the amount of movement of the imaging unit 160 in units of pixels to the amount of movement in units of centimeters and millimeters. For example, one pixel corresponds to 0.1 mm in the vertical direction and 0.1 mm in the horizontal direction on the anterior segment. The XYZ-direction drive control unit 150 thus uses such a relation and converts the amount of movement of the imaging unit 160 in units of pixels to the amount of movement in units of centimeters and millimeters.

The size of the pixel in the image captured by the anterior segment camera 163 can be calculated according to an optical design of the imaging unit 160. For ease of description, it is assumed that the distance from the imaging unit 160 to the subject's eye 170 is approximately constant. If 10 mm on the anterior segment corresponds to 100 pixels on the image, the size of one pixel corresponds to 0.1 mm on the anterior segment. The size in the anterior segment corresponding to one pixel can thus be previously determined.

Further, the XYZ-direction drive control unit 150 determines the amount of movement of the imaging unit 160 in the Z direction using the number of pulses recorded by the UI control unit 120. For example, the amount of movement in the Z direction corresponding to one pulse is previously determined, and the correspondence relation is stored in the memory (not illustrated). In such a case, the correspondence relation regulates the imaging unit 160 so that the imaging unit 160 only moves 1 mm in the Z direction by one pulse. The XYZ-direction drive control unit 150 thus determines the moving distance in the Z direction using the correspondence relation and the number of pulses.

Furthermore, the XYZ-direction drive control unit 150 determines the direction of movement of the imaging unit 160 in the Z direction using the direction of movement of the wheel which has been recorded by the operation unit 140. For example, the XYZ-direction drive control unit 150 determines, if the wheel is rotated towards a near side, the direction of movement as the direction in which the imaging unit 160 moves away from the subject's eye 170. On the other hand, the XYZ-direction drive control unit 150 determines, if the wheel is rotated towards a far side, the direction of movement as the direction in which the imaging unit 160 moves towards the subject's eye 170. However, this is not a limitation.

Moreover, the XYZ-direction drive control unit 150 generates as a voltage control signal, the amount of movement and the direction of movement in the X, Y, and Z directions of the imaging unit 160, using the signal output from the UI control unit 120. For example, the XYZ-direction drive control unit 150 is capable of moving the imaging unit 160 in a positive direction or a negative direction with respect to a predetermined axis, according to a positive or a negative voltage. The XYZ-direction drive control unit 150 then transmits to the Y-direction drive unit 171 the control signal with respect to the Y direction, and transmits to the ZX-direction drive unit 172 the control signals with respect to the X direction and the Z direction. As a result, the XYZ-direction drive control unit 150 causes the Y-direction drive unit 171 and the ZX-direction drive unit 172 to move the imaging unit 160.

The operation performed by the above-described system 1 according to the present exemplary embodiment will be described below with reference to FIG. 3A.

In step S310, the imaging unit 160 captures an image of the anterior segment of the subject's eye and acquires the anterior segment image. The imaging unit 160 then transfers the captured anterior segment image to the UI control unit 120. The UI control unit 120 processes the anterior segment image and causes the display unit 130 to display the anterior segment image. Such a process is an example of a display control process for causing the display unit to display the anterior segment image of the subject's eye captured by the imaging unit. In step S320, the display unit 130 displays the anterior segment image. In step S330, the operator (not illustrated) uses the operation unit 140 to perform an operation on the anterior segment image. The operation unit 140 then outputs to the UI control unit 120 the signal according to the operation by the operator.

In step S340, the UI control unit 120 and the XYZ-direction drive control unit 150 cooperate with each other and calculate the amount of movement of the imaging unit 160 in the X direction and the Y direction. The amount of movement is calculated based on the operation performed by the operator on the anterior segment image, i.e., the signal corresponding to the operation by the operator transmitted from the operation unit 140. In step S350, the UI control unit 120 and the XYZ-direction drive control unit 150 cooperate with each other and calculate the amount of movement of the imaging unit 160 in the Z direction. The amount of movement is calculated based on the operation performed by the operator on the anterior segment image, i.e., the signal corresponding to the operation by the operator transmitted from the operation unit 140. The XYZ-direction drive control unit 150 then converts the amount of movement of the imaging unit 160 in the X, Y, and Z directions calculated in step S340 and S350 to the voltage control signals indicating the amount of movement.

The XYZ-direction drive control unit 150 transmits to the Y-direction drive unit 171 the control signal for the Y direction, and transmits to the ZX-direction drive unit 172 the control signal for the Z direction and the X direction. Such a process is an example of a control process for outputting the control signal indicating the change amount with respect to the imaging unit of the focal position of the anterior segment image in the optical axis direction of the imaging unit.

In step S360, upon receiving the control signal from the XYZ-direction drive control unit 150, the Y-direction drive unit 171 moves the imaging unit 160 in the Y direction according to the amount of movement indicated by the control signal received from the XYZ-direction drive control unit 150. Further, upon receiving the control signal from the XYZ-direction drive control unit 150, the ZX-direction drive unit 172 moves the imaging unit 160 in the Z direction and the X direction according to the amount of movement indicated by the control signal received from the XYZ-direction drive control unit 150. If the operator is to operate on the operation unit 140 again, the processes of step S310 to step S360 are repeatedly performed after the imaging unit 160 is moved. As described above, alignment of the imaging unit 160 is performed with respect to the subject's eye in the three-dimensional direction including the Z direction by only performing the operation on the anterior segment image. The order of performing the processes of step S340 and step S350 may be switched.

The process performed in step S340 illustrated in FIG. 3A will be described in detail below with reference to a flowchart illustrated in FIG. 3B and the anterior segment images illustrated in FIGS. 4A and 4B.

Figure 4B:
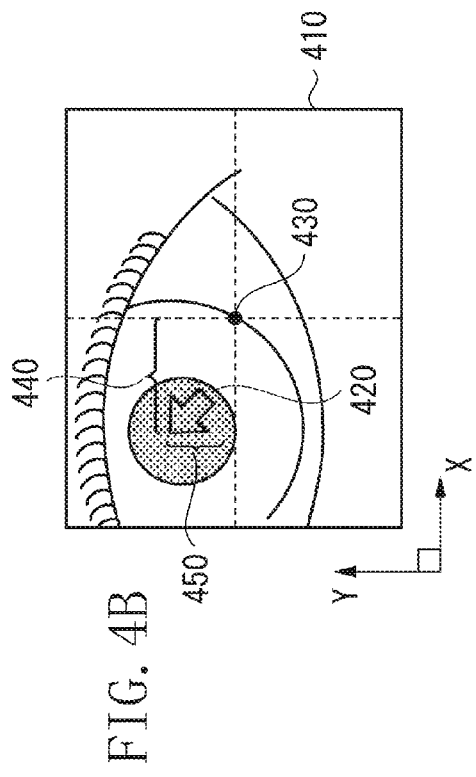
FIGS. 4A, 4B, 4C, and 4D illustrate images of an anterior segment according to the first exemplary embodiment.
Figure 4D:
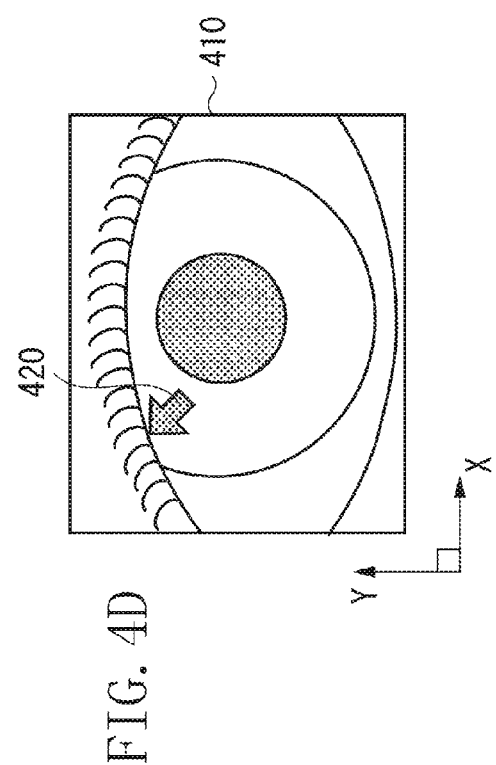
Figure 4A:
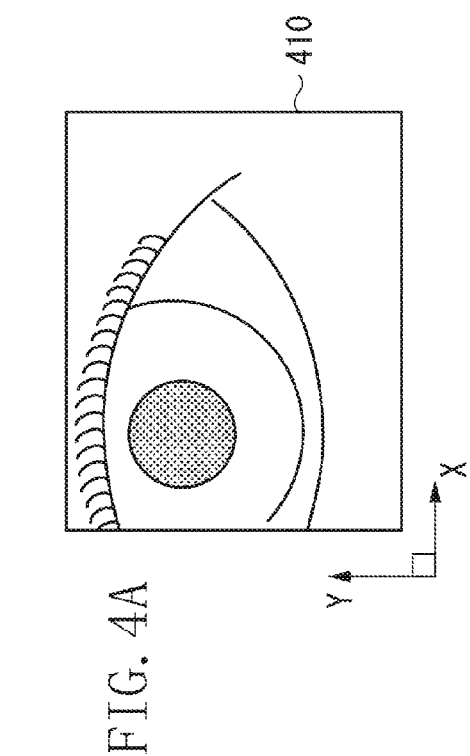

It is assumed that in step S330 illustrated in FIG. 3A, the operator has performed a clicking operation using the operation unit 140, e.g., the mouse, on an anterior segment image 410 displayed on the display unit 130 illustrated FIG. 4A. FIG. 4B illustrates a state of the anterior segment image 410 when the operator has clicked on the image. Referring to FIG. 4B, an arrow 420 indicates the position of a cursor when the operator has clicked the operation unit 140, i.e., the mouse. A target position 430 indicates a center position of the anterior segment image. The target position 430 is not limited to the center position of the anterior segment image and may be other positions. A distance 440 is the distance in the horizontal direction (i.e., the X direction) from the target position 430 to a clicked position indicated by the cursor 420. A distance 450 indicates the distance in the vertical direction (i.e., the Y direction) from the target position 430 to the clicked position indicated by the cursor 420.

Figure 3B:
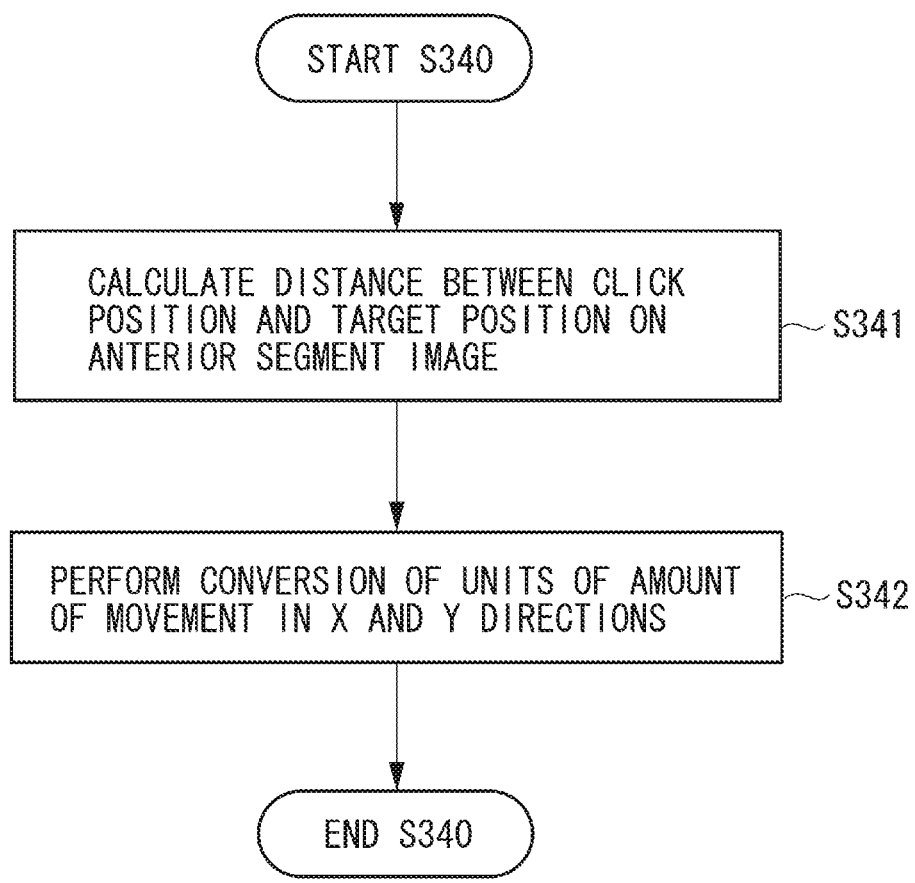

In step S341 illustrated in FIG. 3B, the UI control unit 120 acquires coordinates (Cx, Cy) indicated by the cursor 420. The UI control unit 120 then calculates the distance 440 (Dx) in the horizontal direction and the distance 450 (Dy) in the vertical direction to coordinates (Tx, Ty) of the target position 430. According to the present exemplary embodiment, (Dx, Dy) is expressed as (Dx, Dy)=(Tx, Ty)−(Cx, Cy). The units of (Dx, Dy) are pixels. Further, (Dx, Dy) is not an absolute value, and may be a positive value or a negative value. The imaging unit 160 thus moves in the positive direction or the negative direction with respect to the X direction according to the negative or positive value of (Dx, Dy). The imaging unit 160 similarly moves with respect to the Y direction. In other words, the UI control unit 120 determines the amount of movement of the imaging unit 160 in the X direction and the Y direction.

In step S342, the XYZ-direction drive control unit 150 converts the amount of movement from Dx, Dy whose units are pixels, to the amount of movement of the imaging unit 160 in the X direction and the Y direction in units of centimeters or millimeters. As described above, the size on the anterior segment corresponding to one pixel is determined. The XYZ-direction drive control unit 150 thus uses the correspondence relation and calculates from (Dx, Dy) the amount of movement of the imaging unit 160 in the X direction and the Y direction in units of centimeters or millimeters.

If it is assumed that one pixel corresponds to 0.1 mm in the vertical direction and 0.1 mm in the horizontal direction, an amount of movement (Mx, My) of the imaging unit 160 in the X direction and the Y direction is expressed as (Mx, My)= (Dx, Dy)×0.1. When the amount of movement in centimeters or millimeters is calculated, the process of step S340 ends. The Y-direction drive unit 171 and the ZX-direction drive unit 172 move the imaging unit 160 according to the amounts of movement generated by performing the process of step S342 so that the clicked point matches or approximately matches the target position. More specifically, each of the amounts of movement in the X direction and the Y direction calculated by the XYZ-direction drive control unit 150 is the amount of movement of the imaging unit 160 in the X direction and the Y direction for matching or approximately matching the clicked point to the target position.

Figure 3C:
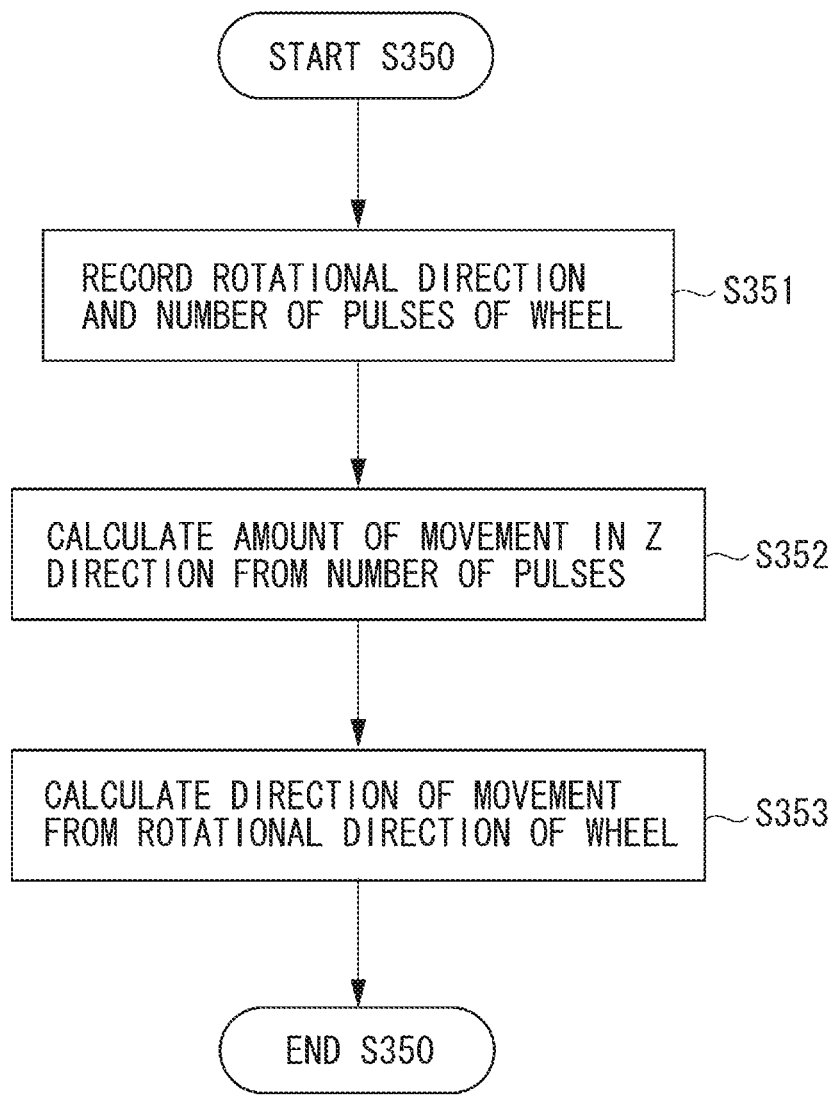

The process performed in step S350 illustrated in FIG. 3A will be described in detail below with reference to a flowchart illustrated in FIG. 3C and the anterior segment images illustrated in FIGS. 4C and 4D.

Figure 4C:
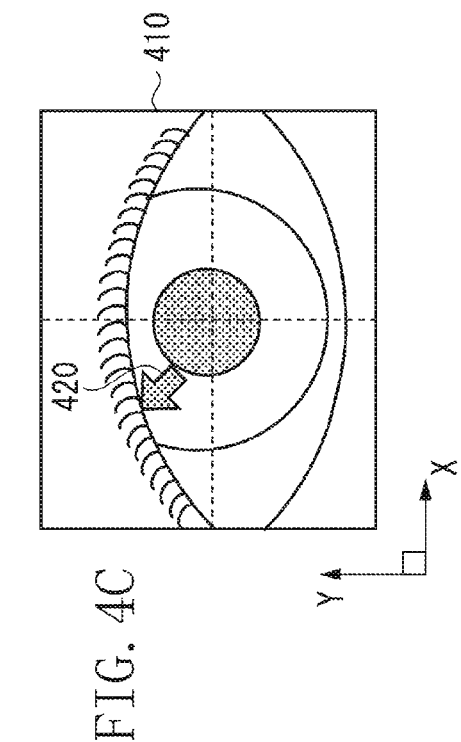

FIG. 4C illustrates the anterior segment image after the imaging unit 160 has moved in the X direction and the Y direction in step S360 illustrated in FIG. 3A. It is assumed that in step S330, the operator has performed the operation for rotating the wheel of the operation unit 140, i.e., the mouse. In step S351, the operation unit 140 outputs to the UI control unit 120 the signal indicating the rotational direction of the wheel and the number of pulses corresponding to the amount of rotation. The UI control unit 120 then receives the signals and records on the memory (not illustrated) the rotational direction of the wheel and the number of pulses. Operation information on the rotational direction of the wheel and the number of pulses may be transmitted to the XYZ-direction drive control unit 150 instead of recording on the memory.

In step S352, the XYZ-direction drive control unit 150 calculates from the number of pulses the amount of movement of the imaging unit 160 in the Z direction. In step S353, the XYZ-direction drive control unit 150 calculates from the rotational direction of the wheel a direction of movement of the imaging unit 160 in the Z direction. The process of step S350 then ends.

FIG. 4D illustrates the anterior segment image 410 displayed on the display unit 130 in step S320 after the ZX-direction drive unit 172 has moved the imaging unit 160 in the Z direction based on the amount of movement and the direction of movement calculated in step S352 and step S353. Referring to FIG. 4D, the imaging unit 160 has moved towards the subject's eye 170.

As described above, according to the present exemplary embodiment, alignment of the imaging unit 160 is performed with respect to the subject's eye 170 in the Z direction (i.e., the depth direction of the subject's eye) by the operation performed on the anterior segment image. Further, alignment of the imaging unit 160 is performed with respect to the subject's eye in the three-dimensional direction including the Z direction by the operation performed on the anterior segment image.

According to the present exemplary embodiment, alignment can be performed in the three-dimensional direction by the operation performed on the anterior segment image. As a result, alignment is less time-consuming as compared to the conventional technique employing a joystick and a mouse, so that the time necessary for performing alignment can be shortened. In other words, according to the present exemplary embodiment, alignment can be more easily performed as compared to the conventional technique.

Further, according to the present exemplary embodiment, alignment is performed when the index is placed on the anterior segment image. It can thus prevent alignment from being unintentionally performed by the operator operating on the operation unit such as a mouse.

According to the first exemplary embodiment, the imaging unit 160 is moved in the X, Y, and Z directions based on the clicking operation and rotation of the wheel. According to a second exemplary embodiment of the present invention, the imaging unit 160 is moved in the X, Y, and Z directions by a different operation. The configuration of the system 1 according to the second exemplary embodiment is approximately similar to the configuration according to the first exemplary embodiment, and detailed description is thus omitted. Further, reference numerals which are similar to those described above indicate portions which are similar or approximately similar.

The operation unit 140 outputs to the UI control unit 120 the operation signal indicating the operation by the operator (not illustrated), according to the operation by the operator. According to the present exemplary embodiment, the operation unit 140 includes a keyboard and a mouse.

The UI control unit 120 receives, when the index which moves according to the movement of the mouse is positioned on the anterior segment image, and the operator moves the mouse while pressing on the button of the mouse (i.e., performs a dragging operation) on the anterior segment image, the operation signal corresponding to the dragging operation. The UI control unit 120 then determines as the amounts of movement of the imaging unit 160 in the X direction and the Y direction, respectively, the amounts of movement of the mouse in the X direction and the Y direction from when the mouse button is pressed to when the mouse button is released (i.e., an amount of dragging). Such an operation of the UI control unit 120 is an operation performed in the case where the operator is not pressing a predetermined key on the keyboard, e.g., a control key, at the same time as performing dragging.

If the operator is pressing a predetermined key on the keyboard, e.g., a control key, at the same time as performing dragging, the UI control unit 120 determines as follows. The UI control unit 120 determines as the amount of movement of the imaging unit 160 in the Z direction the amount of movement of the mouse in the Y direction on the anterior segment image (i.e., vertical direction of the drawing sheet surface) from when the mouse button is pressed to when the mouse button is released. Further, the UI control unit 120 determines as the amount of movement of the imaging unit 160 in the X direction the amount of movement of the mouse in the X direction on the anterior segment image (i.e., the horizontal direction of the drawing sheet surface) from when the mouse button is pressed to when the mouse button is released.

According to the present exemplary embodiment, the amount of dragging is not an absolute value. For example, the amount of dragging indicates a difference between the coordinates on the display unit 130 when the mouse button has been released and the coordinates on the display unit 130 when the mouse button has been pressed. The amount of dragging may be a positive value or a negative value. For example, if the mouse has been dragged from left to right on the anterior segment image, the amount of dragging becomes a positive value. Further, if the mouse has been dragged from the bottom to the top on the anterior segment image, the amount of dragging becomes a positive value.

The key pressed by the operator on the keyboard is not limited to the control key, and may be a shift key or an alt key. Further, it is not necessary to determine, when the operator is pressing a predetermined key in the keyboard, e.g., a control key, at the same time as performing dragging, as the amount of movement of the imaging unit 160 in the X direction, the amount of movement of the mouse in the X direction in the anterior segment image from when the mouse button is pressed to when the mouse button is released. In other words, in such a case, the UI control unit 120 may only determine as the amount of movement of the imaging unit 160 in the Z direction, the amount of movement of the mouse in the Y direction on the anterior segment image (i.e., vertical direction of the drawing sheet surface) from when the mouse button is pressed to when the mouse button is released.

Further, a method of determining the amount of movement of the imaging unit 160 may be reversed between the case where the operator is pressing a predetermined key in the keyboard at the same time as performing dragging, and the case where the operator is not doing so. For example, the UI control unit 120 may determine, when the operator is not pressing the predetermined key on the key board while performing dragging, as the amount of movement of the imaging unit 160 in the Z direction, the amount of movement of the mouse in the Y direction on the anterior segment image from when the mouse button is pressed to when the mouse button is released.

Furthermore, the UI control unit 120 records on the memory (not illustrated) the amount of dragging and a speed of dragging on the anterior segment image, based on the operation signal output from the operation unit 140 according to the operation. Moreover, the UI control unit 120 weights the amount of dragging according to the speed of dragging. More specifically, information in which the speed of dragging is associated with a coefficient is recorded on the memory (not illustrated), and the UI control unit 120 weights the amount of dragging according to the information.

For example, the UI control unit 120 weights the amount of dragging so that the amount of dragging increases as the speed of dragging increases. The UI control unit 120 then outputs to the XYZ-direction drive control unit 150 the weighted signal. The weighting operation may be performed by the XYZ-direction drive control unit 150.

The UI control unit 120 is capable of detecting whether a predetermined key in the keyboard, e.g., a control key, is being pressed, based on the signal output from the operation unit 140.

The XYZ-direction drive control unit 150 converts the signal weighted by the UI control unit 120 to the voltage control signals indicating the amounts of movement of the imaging unit 160 in the X, Y, and Z directions. For example, if the operator is not pressing the control key at the same time as performing dragging, and the amount of dragging in the X direction is a positive value, the XYZ-direction drive control unit 150 generates the control signal which indicates moving the imaging unit 160 in the negative direction with respect to the X direction. According to the present exemplary embodiment, if the amount of dragging with respect to the X direction is a positive value, the operator has dragged the mouse on the display unit 130 from left to right.

Further, if the operator is not pressing the control key at the same time as performing dragging, and the amount of dragging in the Y direction is a positive value, the XYZ-direction drive control unit 150 generates the control signal which indicates moving the imaging unit 160 in the negative direction (i.e., downward direction) with respect to the Y direction. According to the present exemplary embodiment, if the amount of dragging with respect to the Y direction is a positive value, the operator has dragged the mouse on the display unit 130 from the bottom to the top.

Furthermore, if the operator is pressing the control key at the same time as performing dragging, and the amount of dragging in the X direction is a positive value, the XYZ-direction drive control unit 150 generates the control signal which indicates moving the imaging unit 160 in the negative direction with respect to the X direction.

Moreover, if the operator is pressing the control key at the same time as performing dragging, and the amount of dragging in the Y direction is a positive value, the XYZ-direction drive control unit 150 generates the control signal which indicates moving the imaging unit 160 in the positive direction (i.e., the direction towards the subject's eye 170) with respect to the Z direction. The control signals are not limited to those described above. For example, if the operator is pressing the control key at the same time as performing dragging, and the amount of dragging in the Y direction is a positive value, the XYZ-direction drive control unit 150 may generate the control signal which indicates moving the imaging unit 160 in the negative direction (i.e., the direction away from the subject's eye 170) with respect to the Z direction.

The operation performed by the above-described system 1 according to the present exemplary embodiment will be described below with reference to the flowchart illustrated in FIG. 5A.

In step S310, the imaging unit 160 captures an image of the anterior segment of the subject's eye and acquires the anterior segment image. The imaging unit 160 then transmits the captured anterior segment image to the UI control unit 120. The UI control unit 120 processes the anterior segment image and causes the display unit 130 to display the anterior segment image. In step S320, the display unit 130 displays the anterior segment image. In step S330, the operator (not illustrated) uses the operation unit 140 and performs the dragging operation. In step S535, the UI control unit 120 determines whether the control key is being pressing at the same time as performing dragging, based on the operation signal from the operation unit 140.

If the control key is not being pressing at the same time as performing dragging (NO in step S535), the process proceeds to step S540. In step S540, the UI control unit 120 and the XYZ-direction drive control unit 150 cooperate with each other and calculate the amounts of movement of the imaging unit 160 in the X direction and the Y direction, based on the dragging operation performed by the operator on the anterior segment image.

If the control key is being pressing at the same time as performing dragging (YES in step S535), the process proceeds to step S550. In step S550, the UI control unit 120 and the XYZ-direction drive control unit 150 cooperate with each other and calculate the amounts of movement of the imaging unit 160 in the X direction and the Z direction, based on the dragging operation performed by the operator on the anterior segment image.

The XYZ-direction drive control unit 150 then converts the amounts of movement of the imaging unit 160 in the X, Y, and Z directions calculated in step S340 and S350 to the voltage control signals indicating the amounts of movement. The XYZ-direction drive control unit 150 then transmits to the Y-direction drive unit 171 the control signal for the Y direction, and transmits to the ZX-direction drive unit 172 the control signals for the Z direction and the X direction.

In step S360, upon receiving the control signal with respect to the Y direction from the XYZ-direction drive control unit 150, the Y-direction drive unit 171 moves the imaging unit 160 in the Y-direction according to the amount of movement indicated by the control signal received from the XYZ-direction drive control unit 150. Further, upon receiving the control signals with respect to the X direction and the Z direction from the XYZ-direction drive control unit 150, the ZX-direction drive unit 172 moves the imaging unit 160 in the Z direction and the X direction according to the amounts of movement indicated by the control signals received from the XYZ-direction drive control unit 150.

If the operator again performs the operation on the operation unit 140, the processes of step 310 to step S330, step S535, step S535, step S540, step S550, and step S360 are repeatedly performed after the imaging unit 160 has been moved.

Figure 5B:
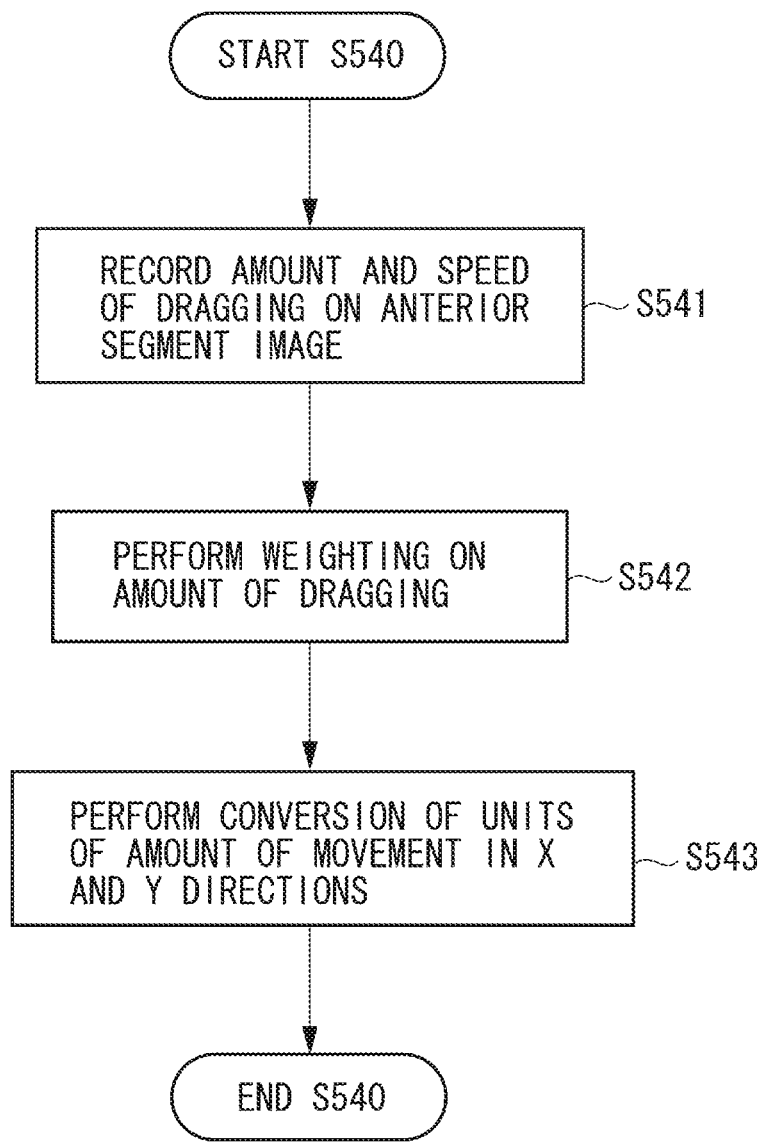

The process performed in step S540 will be described in detail below with reference to the flowchart illustrated in FIG. 5B and the anterior segment images illustrated in FIGS. 6A and 6B.

Figure 6A:
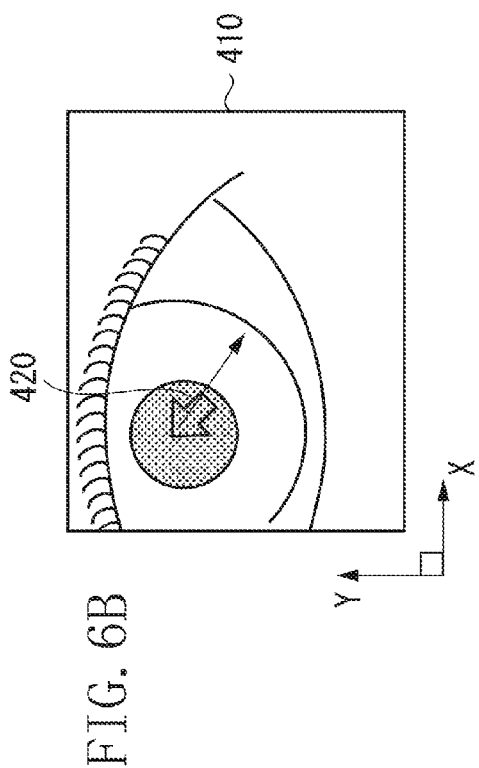
FIGS. 6A, 6B, 6C, and 6D illustrate images of an anterior segment according to the second exemplary embodiment.
Figure 6B:
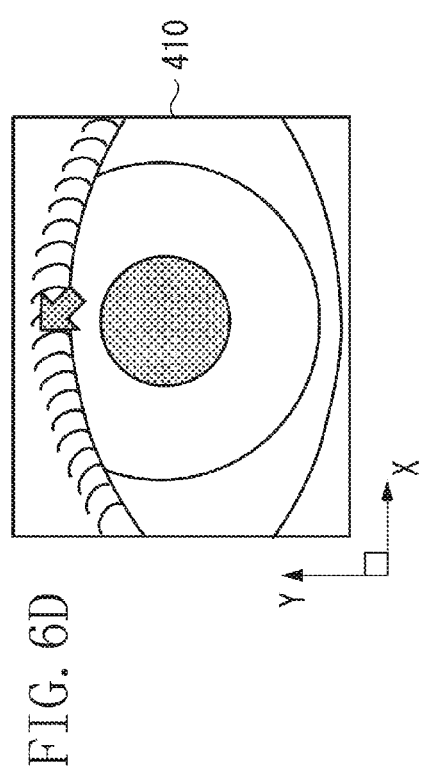

It is assumed that in step S330, the operator has dragged the operation unit 140, e.g., the mouse, on the anterior segment image 410 displayed on the display unit 130 illustrated in FIG. 6A. Referring to FIG. 6B, the operator drags the mouse by moving the mouse from the position of the cursor 420 in the lower right oblique direction. In step S541 illustrated in FIG. 5B, after the dragging operation is performed, the UI control unit 120 receives the operation signal indicating the operation of the operation unit 140. The UI control unit 120 thus calculates and stores in the memory (not illustrated) the amount of dragging and the speed of dragging. The UI control unit 120 can acquire the speed of dragging by dividing the moved distance of the mouse (i.e., a dragging distance) by a period of time the operator has dragged the mouse.

In step S542, the UI control unit 120 weights the amount of dragging using the coefficient corresponding to the speed of dragging. The units of the weighted amount of dragging are pixels, and the weighted amount of dragging indicates the amount of movement of the imaging unit 160. In step S543, the XYZ-direction drive control unit 150 converts the weighted amount of dragging in units of pixels (i.e., amount of movement) to the amounts of movement of the imaging unit 160 in the X direction and the Y direction in units of centimeters and millimeters. Upon calculation of the amounts of movement in units of centimeters and millimeters, the process ends.

The process performed in step S550 will be described in detail below with reference to the flowchart illustrated in FIG. 5C and the anterior segment images illustrated in FIGS. 6C and 6D.

Figure 6C:
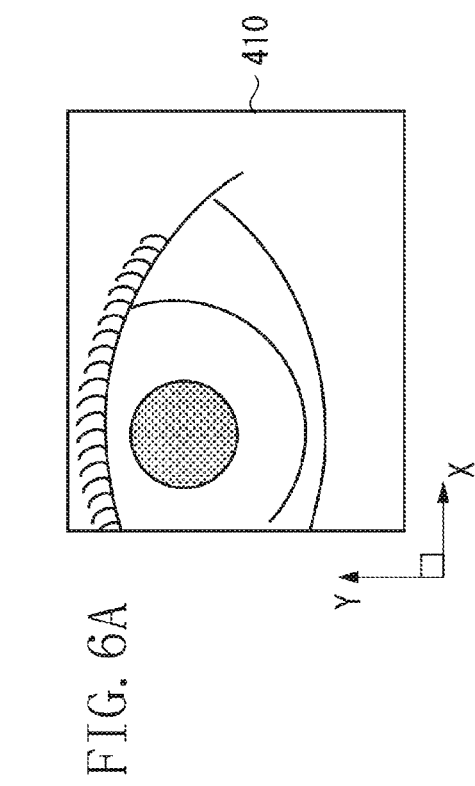

FIG. 6C illustrates the anterior segment image after the imaging unit 160 has moved in the X direction and the Y direction according to the dragging operation in step S360 illustrated in FIG. 3A. It is assumed that in step S330, the operator has performed the dragging operation in the upper direction (i.e., Y direction) on the anterior segment image as illustrated in FIG. 6C.

In step S551 illustrated in FIG. 5C, the UI control unit 120 then receives the operation signal indicating the operation of the operation unit 140, so that the UI control unit 120 calculates and stores in the memory (not illustrated) the amount of dragging and the speed of dragging. In step S552, the UI control unit 120 weights the amount of dragging using the coefficient corresponding to the speed of dragging. The weighted amount of dragging which is in units of pixels indicates the amount of movement of the imaging unit 160. In step S553, the XYZ-direction drive control unit 150 converts the weighted amount of dragging in units of pixels (i.e., amount of movement) to the amounts of movement of the imaging unit 160 in the Z direction and the X direction in units of centimeters and millimeters. Upon calculation of the amounts of movement in units of centimeters and millimeters, the process of step S550 ends. Since the operator does not perform dragging in the X direction in FIG. 6C, the amount of movement in the X direction becomes 0.

Figure 6D:
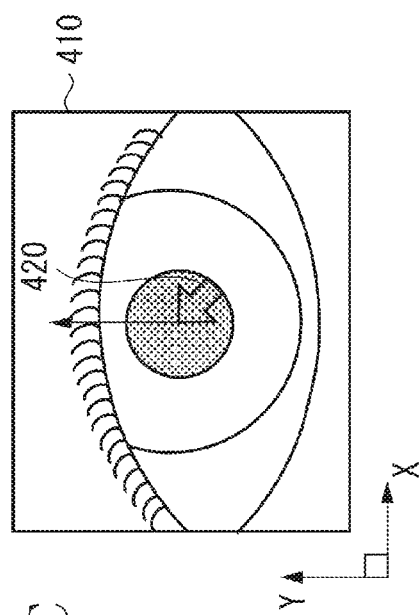

FIG. 6D illustrates the anterior segment image 410 displayed on the display unit 130 in step S320 illustrated in FIG. 5A after the ZX-direction drive unit 172 has moved the imaging unit 160 in the Z direction based on the amount of movement calculated in step S553.

The processes performed in step S542 and step S552 may be omitted. In other words, it is not necessary to perform weighting. Further, the processes of step S541 and step S551 may be performed prior to the process of step S535. Furthermore, the processes of step S542 and step S552 may be performed prior to the process of step S535.

As described above, according to the present exemplary embodiment, similar results as the first exemplary embodiment can be acquired. Further, since the operation using the mouse can perform alignment in the three-dimensional direction by only a single operation (i.e., the dragging operation), alignment can be easily performed.

According to a third exemplary embodiment of the present invention, a predetermined area is set in the anterior segment image displayed on the display unit 130. The imaging unit 160 is then moved in the X, Y, and Z directions according to whether the operation is an operation performed in the predetermined area. The configuration of the system 1 according to the second exemplary embodiment is approximately similar to the configuration according to the first exemplary embodiment, and detailed description is thus omitted. Further, reference numerals which are similar to those described above indicate portions which are similar or approximately similar.

The UI control unit 120 displays the predetermined area on an arbitrary position in the anterior segment image displayed on the display unit 130. Since the UI control unit 120 recognizes the coordinates of the predetermined area, the UI control unit 120 can determine whether the index which moves according to the movement of the mouse is positioned in the predetermined area. As a result, the UI control unit 120 can determine whether a start position of dragging using the operation unit, e.g., the mouse, is in the predetermined area.

Further, the UI control unit 120 receives, if the operator moves the mouse on the anterior segment image while pressing the mouse button (i.e., performs the dragging operation), the operation signal corresponding to the dragging operation. If the index which moves along with the movement of the mouse is positioned outside the predetermined area on the anterior segment image when the dragging operation is started, the UI control unit 120 determines the amount of movement as follows. The UI control unit 120 determines as the amounts of movement of the imaging unit 160 in the X direction and the Y direction, respectively, the amounts of movement of the mouse in the X direction and the Y direction from when the mouse button is pressed to when the mouse button is released (i.e., the amount of dragging).

Furthermore, if the index is positioned in the predetermined area when the dragging operation is started, the UI control unit 120 determines as follows. The UI control unit 120 determines as the amount of movement of the imaging unit 160 in the Z direction, the amount of movement of the mouse in the Y direction (i.e., the vertical direction of the drawing sheet surface) from when the mouse button is pressed to when the mouse button is released. Moreover, in such a case, the UI control unit 120 determines as the amount of movement of the imaging unit 160 in the X direction, the amount of movement of the mouse in the X direction (i.e., the horizontal direction of the drawing sheet surface) from when the mouse button is pressed to when the mouse button is released.

It is not necessary in the above-described case to determine as the amount of movement of the imaging unit 160 in the X direction the amount of movement of the mouse in the X direction from when the mouse button is pressed to when the mouse button is released. In other words, when the index is positioned in the predetermined area when the dragging operation is started, the UI control unit 120 may only determine as the amount of movement of the imaging unit 160 in the Z direction, the amount of movement of the mouse in the Y direction from when the mouse button is pressed to when the mouse button is released.

The method for determining the amount of movement of the imaging unit 160 may be reversed between the case where the index is positioned in the predetermined area when the dragging operation is started, and the case where the index is positioned outside the predetermined area on the anterior segment image when the dragging operation is started. For example, if the index is positioned outside the predetermined area on the anterior segment image when the dragging operation is started, the UI control unit 120 may determine as follows. The UI control unit 120 may determine as the amount of movement of the imaging unit 160 in the Z direction, the amount of movement of the mouse in the Y direction from when the mouse button is pressed to when the mouse button is released.

Further, the UI control unit 120 records on the memory (not illustrated) the amount of dragging and the speed of dragging on the anterior segment image, based on the operation signal output from the operation unit 140 according to the operation. Furthermore, the UI control unit 120 weights the amount of dragging according to the speed of dragging. More specifically, the information in which the speed of dragging is associated with a coefficient is recorded on the memory (not illustrated), and the UI control unit 120 weights the amount of dragging according to the information. For example, the UI control unit 120 weights the amount of dragging so that the amount of dragging increases as the speed of dragging increases. The UI control unit 120 then outputs to the XYZ-direction drive control unit 150 the weighted signal. The weighting operation may be performed by the XYZ-direction drive control unit 150.

The XYZ-direction drive control unit 150 converts the signals weighted by the UI control unit 120 to the voltage control signals indicating the amounts of movement of the imaging unit 160 in the X, Y, and Z directions. For example, if the index is positioned outside the predetermined area on the anterior segment image when the dragging operation is started, and the amount of dragging in the X direction is a positive value, the XYZ-direction drive control unit 150 generates the control signal which indicates moving the imaging unit 160 in the negative direction with respect to the X direction. Further, if the index is positioned outside the predetermined area on the anterior segment image when the dragging operation is started, and the amount of dragging in the Y direction is a positive value, the XYZ-direction drive control unit 150 generates the control signal which indicates moving the imaging unit 160 in the negative direction with respect to the Y direction.

Furthermore, if the index is positioned in the predetermined area when the dragging operation is started, and the amount of dragging in the X direction is a positive value, the XYZ-direction drive control unit 150 generates the control signal which indicates moving the imaging unit 160 in the negative direction with respect to the X direction. Moreover, if the index is positioned in the predetermined area when the dragging operation is started, and the amount of dragging in the Y direction is a positive value, the XYZ-direction drive control unit 150 generates the control signal which indicates moving the imaging unit 160 in the positive direction (i.e., the direction towards the subject's eye 170) with respect to the Z direction. The control signals are not limited to those described above. For example, if the index is positioned in the predetermined area when the dragging operation is started, and the amount of dragging in the Y direction is a positive value, the XYZ-direction drive control unit 150 may generate the control signal which indicates moving the imaging unit 160 in the negative direction (i.e., the direction away from the subject's eye 170) with respect to the Z direction.

The operation performed by the above-described system 1 according to the present exemplary embodiment will be described below with reference to the flowchart illustrated in FIG. 7A.

In step S310, the imaging unit 160 captures an image of the anterior segment of the subject's eye and acquires the anterior segment image. The imaging unit 160 then transfers the captured anterior segment image to the UI control unit 120. The UI control unit 120 processes the anterior segment image and causes the display unit 130 to display the anterior segment image. In step S320, the display unit 130 displays the anterior segment image. In step S725, the UI control unit 120 causes the display unit 130 to display a ZX operation area, which is the predetermined area, superimposed on the anterior segment image. In step S330, after the anterior segment image and the ZX operation area are displayed on the display unit 130, the operator (not illustrated) uses the operation unit 140 and performs the dragging operation. In step S735, the UI control unit 120 determines whether the dragging start position is within the ZX operation area.

If the UI control unit 120 determines that the dragging start position is outside the ZX operation area (NO in step S735), the process proceeds to step S740. In step S740, the UI control unit 120 and the XYZ-direction drive control unit 150 cooperate with each other and calculate the amounts of movement of the imaging unit 160 in the X direction and the Y direction, based on the dragging operation performed by the operator on the anterior segment image.

If the dragging start position is within the ZX operation area (YES in step S735), the process proceeds to step S750. In step S750, the UI control unit 120 and the XYZ-direction drive control unit 150 cooperate with each other and calculate the amounts of movement of the imaging unit 160 in the X direction and the Z direction, based on the dragging operation performed by the operator on the anterior segment image.

The XYZ-direction drive control unit 150 then converts the amounts of movement of the imaging unit 160 in the X, Y, and Z directions calculated in step S740 and S750 to the voltage control signals which indicate the amounts of movement. The XYZ-direction drive control unit 150 transmits to the Y-direction drive unit 171 the control signal for the Y direction, and transmits to the ZX-direction drive unit 172 the control signals for the Z direction and the X direction.

In step S360, upon receiving the control signal with respect to the Y direction from the XYZ-direction drive control unit 150, the Y-direction drive unit 171 moves the imaging unit 160 in the Y direction according to the amount of movement indicated by the control signal received from the XYZ-direction drive control unit 150. Further, upon receiving the signal with respect to the X direction and the Z direction from the XYZ-direction drive control unit 150, the ZX-direction drive unit 172 moves the imaging unit 160 in the Z direction and the X direction according to the amounts of movement indicated by the control signals received from the XYZ-direction drive control unit 150.

If the operator again performs the operation on the operation unit 140, the processes of step 310 to step S330, step S725, step S735, step S740, step S750, and step S360 are repeatedly performed after the imaging unit 160 is moved.

The process performed in step S740 will be described in detail below with reference to the flowchart illustrated in FIG. 7B and the anterior segment images illustrated in FIGS. 8A and 8B.

Figure 7A:
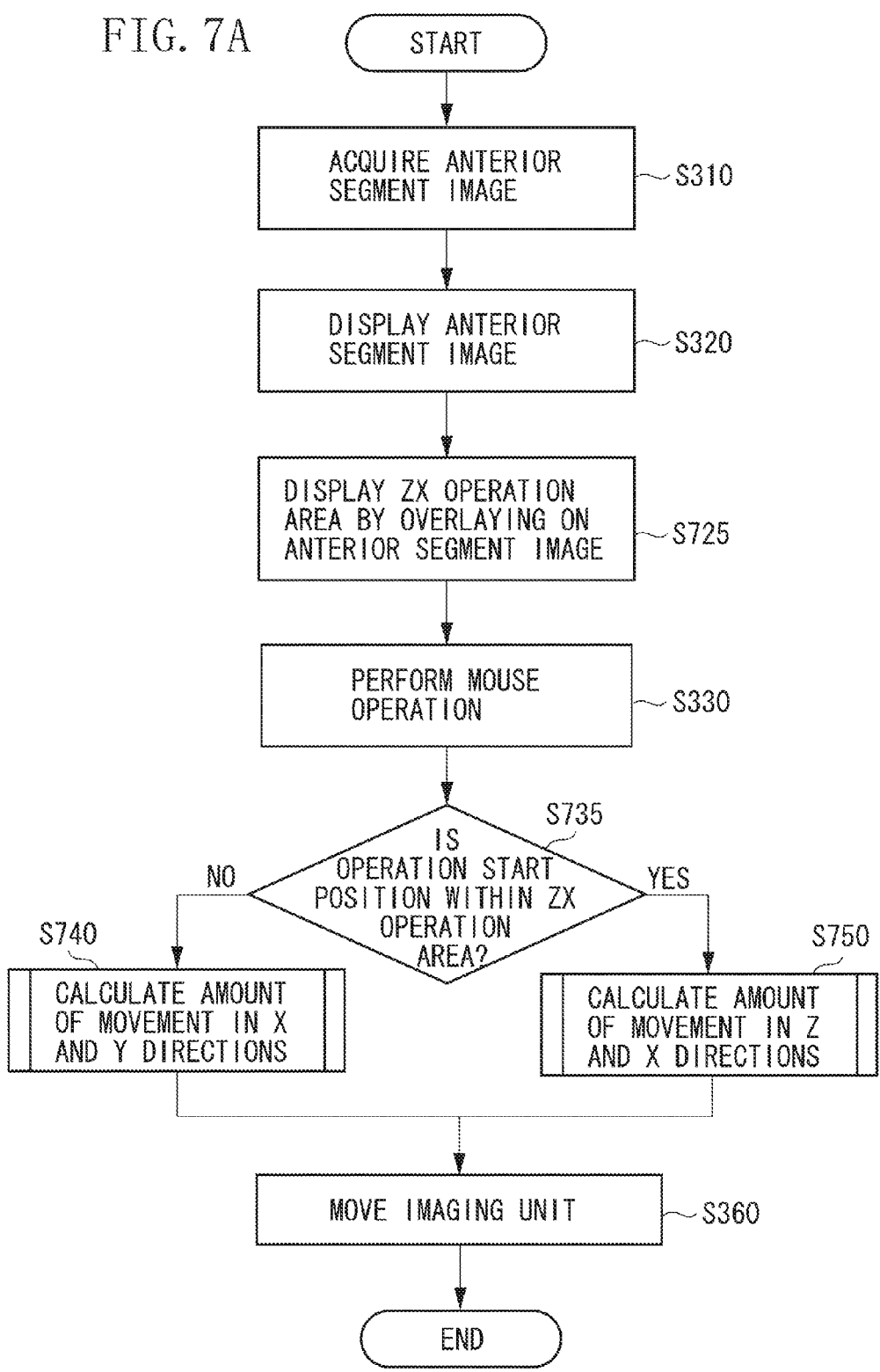
Figure 8A:
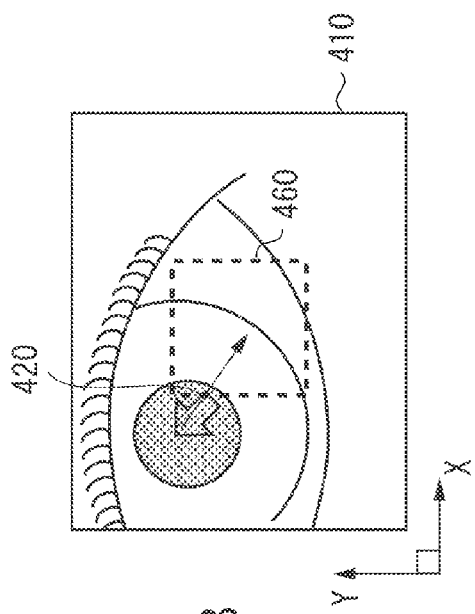
FIGS. 8A, 8B, 8C, and 8D illustrate images of an anterior segment according to the third exemplary embodiment.
Figure 8B:
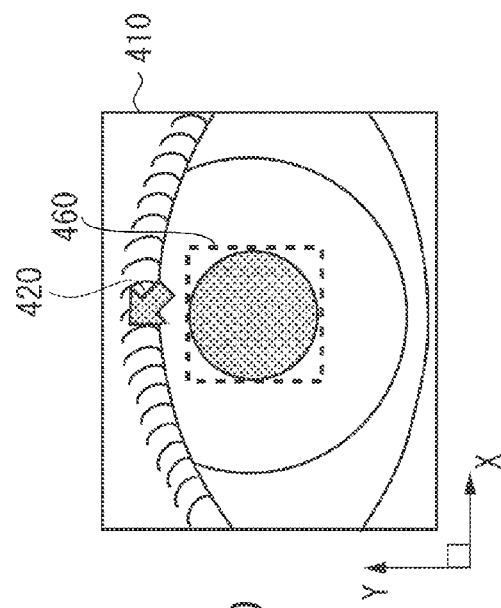

In step S725 illustrated in FIG. 7A, a ZX operation area 460 is displayed on the anterior segment image 410 on the display unit 130 as illustrated in FIG. 8A. For example, as illustrated in FIG. 8B, it is assumed that the dragging operation is performed by moving the mouse from the position of the cursor 420 in the lower right oblique direction. In step S741 illustrated in FIG. 7B, after the dragging operation is performed, the UI control unit 120 receives the operation signal indicating the operation of the operation unit 140. The UI control unit 120 then calculates and stores in the memory (not illustrated) the amount of dragging and the speed of dragging. The UI control unit 120 can acquire the speed of dragging by dividing the moved distance of the mouse (i.e., a dragging distance) by a period of time the mouse has been dragged.

In step S742, the UI control unit 120 weights the amount of dragging using the coefficient corresponding to the speed of dragging. The units of the weighted amount of dragging are pixels, and the weighted amount of dragging indicates the amount of movement of the imaging unit 160. In step S743, the XYZ-direction drive control unit 150 converts the weighted amount of dragging (i.e., the amount of movement) in terms of pixels to the amounts of movement of the imaging unit 160 in the X direction and the Y direction in units of centimeters and millimeters. Upon calculation of the amounts of movement in units of centimeters and millimeters, the process of step S740 ends.

The process performed in step S750 will be described in detail below with reference to the flowchart illustrated in FIG. 7C and the anterior segment images illustrated in FIGS. 8C and 8D.

Figure 8C:
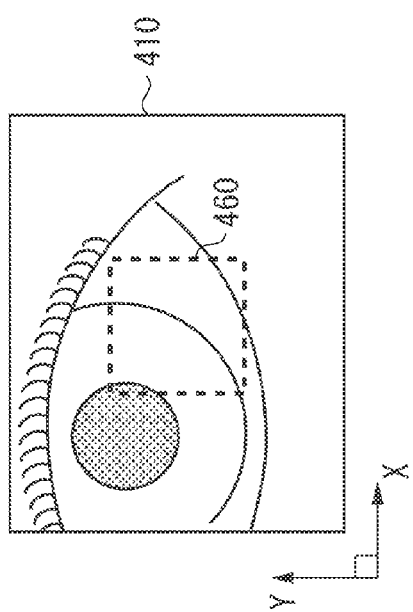

FIG. 8C illustrates the anterior segment image after the imaging unit 160 has moved in the X direction and the Y direction according to the dragging operation in step S360 illustrated in FIG. 7A. It is assumed that in step S330, the dragging operation is performed in the upper direction (i.e., Y direction) on the anterior segment image as illustrated in FIG. 8C, from the dragging start position within the ZX operation area 460. In step S751 illustrated in FIG. 7C, the UI control unit 120 then receives the operation signal indicating the operation of the operation unit 140, so that the UI control unit 120 calculates and stores in the memory (not illustrated) the amount of dragging and the speed of dragging.

In step S752, the UI control unit 120 weights the amount of dragging using the coefficient corresponding to the speed of dragging. The weighted amount of dragging which is in units of pixels indicates the amount of movement of the imaging unit 160. In step S753, the XYZ-direction drive control unit 150 converts the weighted amount of dragging (i.e., amount of movement) in units of pixels to the amounts of movement of the imaging unit 160 in the Z direction and the X direction in units of centimeters and millimeters. When the amounts of movement in units of centimeters and millimeters are calculated, the process of step S750 ends. Since the dragging operation is not performed in the X direction in FIG. 8C, the amount of movement in the X direction becomes 0.

Figure 8D:
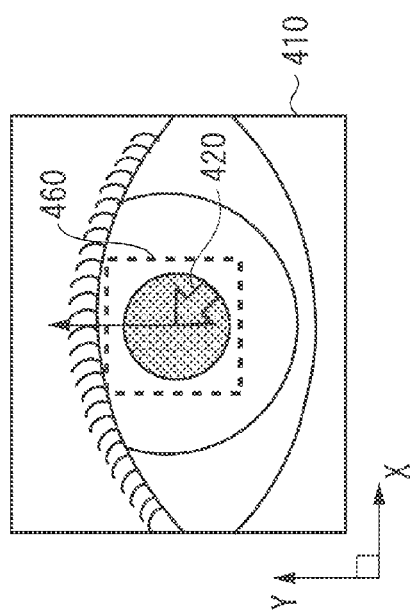

FIG. 8D illustrates the anterior segment image displayed on the display unit 130 in step S320 illustrated in FIG. 5A after the ZX-direction drive unit 172 has moved the imaging unit 160 in the Z direction based on the amount of movement calculated in step S753.

The processes performed in step S742 and step S752 may be omitted. In other words, it is not necessary to perform weighting. Further, the processes of step S741 and step S751 may be performed previous to the process of step S735. Furthermore, the processes of step S742 and step S752 may be performed previous to the process of step S735.

As described above, according to the present exemplary embodiment, similar results as the first exemplary embodiment can be acquired. Further, the operation using the mouse can perform alignment in the three-dimensional direction by only a single operation (i.e., a dragging operation), so that alignment in the three-dimensional direction can be easily performed.

According to a fourth exemplary embodiment of the present invention, an image area in the anterior segment image generated by light transmitted through a prism lens 184 (i.e., a splitter area) to be described below is set as the ZX operation area described in the third exemplary embodiment.

FIG. 9 illustrates the configuration of the imaging unit 160 according to the fourth exemplary embodiment. Referring to FIG. 9, the imaging unit 160 includes the anterior segment-illumination light emitting diodes (LED) 161a and 161b, the objective lens 162, the anterior segment camera 163, and the prism lens 184. Reference numerals which are similar to those described above indicate portions which are similar or approximately similar.

The prism lens 184 is used for adjusting the distance between the subject's eye 170 and the objective lens 162. In other words, the prism lens 184 is used for adjusting with respect to the anterior segment camera 163 the focal position of the anterior segment image in the optical axis direction of the anterior segment camera 163. The prism lens 184 includes two prisms of different inclinations. If the distance between the subject's eye 170 and the objective lens 162 are not appropriately aligned, the anterior segment image generated by the light transmitted through the prism lens is displaced in left and right directions as illustrated in FIG. 10C to be described below. There is no displacement as described above in the anterior segment image generated by the light that is not transmitted through the prism lens. The prism lens 184 may be realized by various known methods, so that detailed description will be omitted.

The UI control unit 120 causes the display unit 130 to display, based on the area in which the displacement is generated in the image (i.e., a splitter area) on the anterior segment image displayed on the display unit 130, the image indicating the area in which the displacement is generated. The area on the anterior segment image in which the displacement is generated in the image can be previously acquired based on the size of the prism lens 184 and the optical design of the imaging unit 160. The area in which the displacement is generated can be stored in the memory (not illustrated). As a result, the UI control unit 120 can cause the display unit 130 to display, by referring to the memory, the image indicating the area in which the displacement is generated in the image on the anterior segment image.

According to an example in the present exemplary embodiment, the ZX operation area according to the third exemplary embodiment is only replaced by the area in which the image becomes divided by the splitter. The operation of the system 1 is similar or approximately similar to that described in FIGS. 7A, 7B, and 7C, so that detailed description will be omitted.

FIGS. 10A, 10B, 10C, and 10D illustrate the anterior segment images in the case where the operations approximately similar to the operations performed with respect to the anterior segment images illustrated in FIGS. 8A, 8B, 8C, and 8D are performed.

Figure 10A:
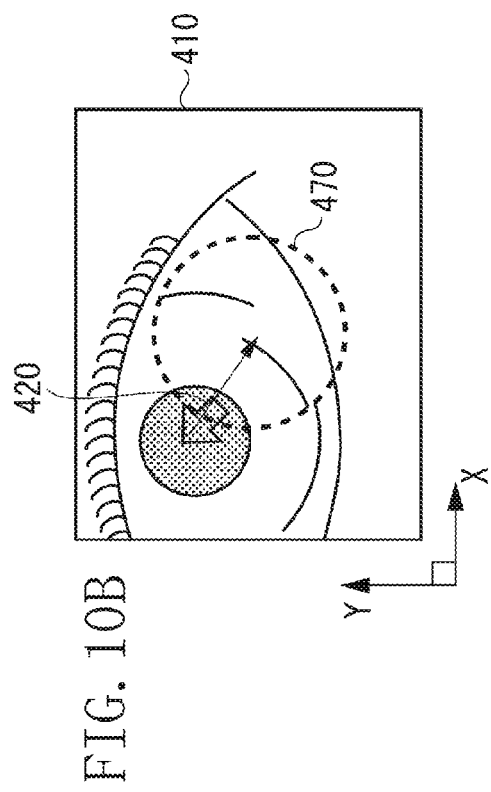
FIGS. 10A, 10B, 10C, and 10D illustrate images of an anterior segment according to the fourth exemplary embodiment.

FIG. 10A illustrates a state in which a ZX operation area 470 is displayed in the area in which the displacement is generated by the prism lens 184 in the image (i.e., a split area) on the anterior segment image.

Figure 10B:
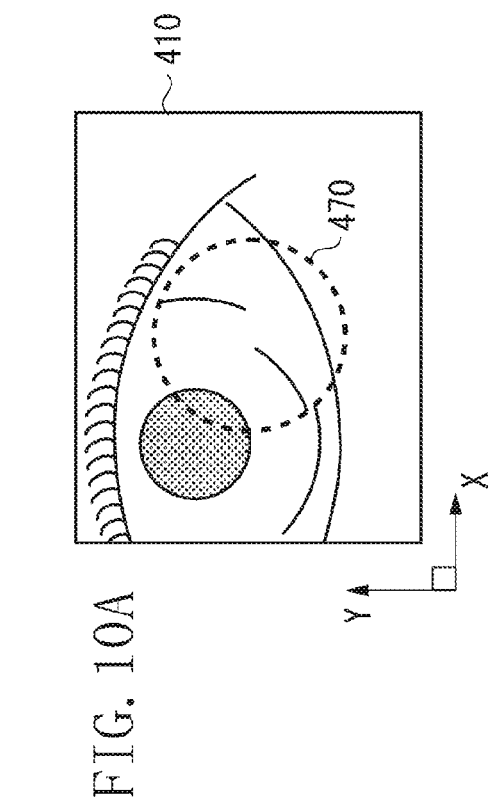
Figure 10C:
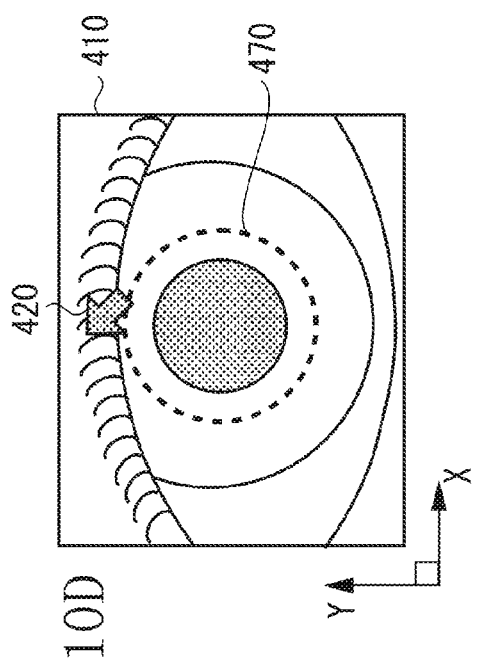

FIG. 10B illustrates the dragging operation performed from the position outside the ZX operation area 470 corresponding to the split area in the lower right oblique direction.

Figure 10D:
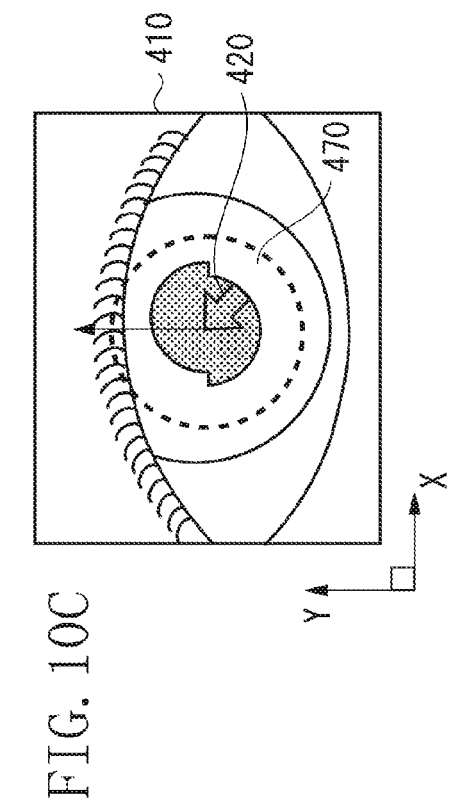

As a result of performing the dragging operation, the imaging unit 160 moves in the X and Y directions, similarly as described in the third exemplary embodiment. The display unit 130 then displays the anterior segment image illustrated in FIG. 10C. Since the distance between the subject's eye and the objective lens 162 is not appropriate in FIG. 10C, the image is displaced to the left and the right in the ZX operation area 470 corresponding to the split area. The dragging operation is then performed from the position within the ZX operation area 470 corresponding to the split area to the Y direction as illustrated in FIG. 10C. By performing the dragging operation in the Y direction, the imaging unit 160 is moved in the Z direction according to the amount of dragging. FIG. 10D illustrates the state in which there is no displacement in the image in the ZX operation area 470 corresponding to the split area as a result of moving the imaging unit 160 in the Z direction, so that appropriate alignment is performed.

According to the present exemplary embodiment, the result similar to the third exemplary embodiment is acquired. Further, since alignment in the Z direction can be performed from the operation unit 140 while viewing the displacement of the image generated due to the prism lens 184, alignment in the Z direction can be more easily performed.

The present invention may also be realized by supplying to a system or an apparatus via a network (so as a signal) or various storage media, software (i.e., a program code) for implementing the function of the above-described exemplary embodiments, and a computer (or a CPU or a micro processing unit (MPU)) in the system or the apparatus reading and executing the program code.

According to the above-described exemplary embodiments, alignment with respect to the subject's eye 170 is performed by moving the imaging unit 160 in the X, Y and Z directions. In other words, the imaging unit 160 is moved in the Z direction so that the focal position of the image of the eye is moved in the optical axis direction of the imaging unit 160 with respect to the anterior segment camera 163. However, the present invention is not limited to the above. For example, a drive unit (not illustrated) may move the objective lens 162 in the imaging unit 160 in the optical axis direction of the imaging unit 160 so that the focal position of the image of the eye is moved in the optical axis direction of the imaging unit 160 with respect to the anterior segment camera 163. Further, a focus lens may be included between the objective lens 162 and the anterior segment camera 163 in the imaging unit 160. The drive unit (not illustrated) then moves the focus lens in the optical axis direction of the imaging unit 160, so that the focal position of the image of the eye is moved in the optical axis direction of the imaging unit 160 with respect to the anterior segment camera 163.

Furthermore, according to the above-described exemplary embodiments, alignment with respect to the subject's eye 170 is performed by moving the imaging unit 160 in the X, Y and Z directions. However, the present invention is not limited to the above, and alignment may be performed by moving in the X, Y and Z directions a jaw rest (not illustrated) on which a subject places the jaw.

Moreover, according to the above-described exemplary embodiments, the mouse is employed as the operation unit 140, and the amount of movement of the imaging unit 160 is determined based on operations such as clicking, dragging, and rotation of the wheel. However, the operations performed using the operation unit 140 are not limited to the above. For example, the amount of movement of the imaging unit 160 may be determined based on a double-clicking operation.

Further, according to the above-described exemplary embodiments, the ophthalmologic apparatus includes the imaging unit 160, the Y-direction drive unit 171, and the ZX-direction drive unit 172. However, the configuration of the ophthalmologic apparatus is not limited to the above. For example, the ophthalmologic apparatus may include all or a portion of the XYZ-direction drive control unit 150.

Furthermore, a scroll bar for causing the XYZ-direction drive control unit 150 to move the imaging unit 160 may be displayed along with the anterior segment image displayed on the display unit illustrated in FIGS. 4A, 4B, 4C, and 4D. If the scroll bar is moved by dragging the operation unit 140, the XYZ-direction drive control unit 150 generates the control signal indicating the amount of movement of the imaging unit 160 according to the amount of movement of the scroll bar. The ZX-direction drive unit 172 then moves the imaging unit 160 in the Z direction based on the control signal. Moreover, if the imaging unit 160 moves in the Z direction along with the movement of the wheel in the operation unit 140 on the anterior segment image, the scroll bar may move along with the movement of the imaging unit 160 in the Z direction. The position to which the imaging unit 160 has moved can thus be acquired by referring to the scroll bar.

Further, the scroll bar may be displayed in any of the left, right, up, and down directions of the anterior segment image displayed on the display unit 130. Furthermore, "subject (examinee) side" and "examiner side" may be displayed on both ends of the scroll bar to clarify the direction in which the imaging unit 160 is to be moved by moving the scroll bar. As a result, the position to which the imaging unit 160 is moved can be more easily acquired by referring to the scroll bar.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2011-079365 filed Mar. 31, 2011, which is hereby incorporated by reference herein in its entirety.

What is claimed is:

1. A control apparatus comprising:
    a display control unit configured to cause a display unit to display an image of an anterior segment of a subject's eye captured by an imaging unit;
    a recognition unit configured to recognize whether an index indicating a portion on the display unit is located on the image of the anterior segment; and
    a control unit configured to output, based on an operation signal output from an output unit according to an operation on the operation unit when the recognition unit recognizes that an index indicating an arbitrary position on the display unit is located on the image of the anterior segment, a control signal indicating a change amount in an optical axis direction of the imaging unit of a focal position of the image of the anterior segment relative to the imaging unit,
    wherein a position of the index is changeable by the operation unit.

2. The control apparatus according to claim 1, wherein the control unit is configured to output, based on the operation signal, a control signal indicating an amount of movement of the imaging unit in the optical axis direction of the imaging unit according to an operation on the operation unit.

3. The control apparatus according to claim 2, wherein the control unit is configured to output the control signal to a changing unit, which is configured to move the imaging unit, to cause the changing unit to move the imaging unit in the optical axis direction of the imaging unit.

4. The control apparatus according to claim 1, wherein the control unit is configured to output, based on the operation signal output from the operation unit according to an operation on the operation unit when the index is located on the image of the anterior segment, a control signal indicating a change amount in a positional relationship between the subject's eye and the imaging unit in a planar direction perpendicular to the optical axis direction of the imaging unit.

5. The control apparatus according to claim 4, wherein the control unit is configured to output, based on the operation signal, a control signal indicating an amount of movement of the imaging unit in the planar direction perpendicular to the optical axis direction of the imaging unit according to an operation on the operation unit.

6. The control apparatus according to claim 5, wherein the control unit is configured to output the control signal to a changing unit, which is configured to move the imaging unit, to cause the changing unit to move the imaging unit in the planar direction perpendicular to the optical axis direction of the imaging unit.

7. The control apparatus according to claim 1,
    wherein the operation unit includes a first operation portion and a second operation portion, and
    wherein when the recognition unit recognizes that an index indicating an arbitrary position on the display unit is located on the image of the anterior segment, the control unit is configured to output, based on an operation signal output from the operation unit according to an operation on the first operation portion, a control signal indicating a change amount in an optical axis direction of the imaging unit of a focal position of the image of the anterior segment relative to the imaging unit, and to output, based on an operation signal output from the operation unit according to an operation on the second operation portion, a control signal indicating a change amount on a plane perpendicular to the optical axis direction of the imaging unit.

8. The control apparatus according to claim 7, wherein the operation unit is a mouse, the first operation portion is a wheel, and the second operation portion is a button.

9. An ophthalmologic apparatus comprising:
    an imaging unit configured to capture an image of an anterior segment of a subject's eye;
    a recognition unit configured to recognize whether an index indicating a portion on a display unit is located on the image of the anterior segment displayed on the display unit; and
    a changing unit configured to change a focal position of the image of the anterior segment relative to the imaging unit in an optical axis direction of the imaging unit based on a control signal output from a control unit according to an operation on an operation unit when the recognition unit recognizes that the index is located on the image of the anterior segment displayed on the display unit,
    wherein a position of the index is changeable by the operation unit.

10. The ophthalmologic apparatus according to claim 9,
    wherein the operation unit includes a first operation portion and a second operation portion, and
    wherein when the recognition unit recognizes that an index indicating an arbitrary position on the display unit is located on the image of the anterior segment, the control unit is configured to output, based on an operation signal output from the operation unit according to an operation on the first operation portion, a control signal indicating a change amount in an optical axis direction of the imaging unit of a focal position of the image of the anterior segment relative to the imaging unit, and to output, based on an operation signal output from the operation unit according to an operation on the second operation portion, a control signal indicating a change amount on a plane perpendicular to the optical axis direction of the imaging unit.

11. The ophthalmologic apparatus according to claim 10, wherein the operation unit is a mouse, the first operation portion is a wheel, and the second operation portion is a button.

12. A system comprising:
    an imaging unit configured to capture an image of an anterior segment of a subject's eye;
    a display unit configured to display the image of the anterior segment;
    a recognition unit configured to recognize whether an index indicating a portion on the display unit is located on the image of the anterior segment;
    a control unit configured to output, based on an operation signal output from an operation unit according to an operation on the operation unit when the recognition unit recognizes that the index is located on the image of the anterior segment, a control signal indicating a change amount in an optical axis direction of the imaging unit of a focal position of the image of the anterior segment relative to the imaging unit; and a changing unit configured to change the focal position in the optical axis direction of the imaging unit based on the control signal, wherein a position of the index is changeable by the operation unit.

13. The system according to claim 12, wherein the operation unit includes a first operation portion and a second operation portion, and wherein when the recognition unit recognizes that an index indicating an arbitrary position on the display unit is located on the image of the anterior segment, the control unit is configured to output, based on an operation signal output from the operation unit according to an operation on the first operation portion, a control signal indicating a change amount in an optical axis direction of the imaging unit of a focal position of the image of the anterior segment relative to the imaging unit, and to output, based on an operation signal output from the operation unit according to an operation on the second operation portion, a control signal indicating a change amount on a plane perpendicular to the optical axis direction of the imaging unit.

14. The system according to claim 13, wherein the operation unit is a mouse, the first operation portion is a wheel, and the second operation portion is a button.

15. A control method comprising:

causing a display unit to display an image of an anterior segment of a subject's eye captured by an imaging unit;

recognizing whether an index indicating a portion on the display unit is located on the image of the anterior segment; and outputting, based on an operation signal output from an operation unit according to an operation on the operation unit when it is recognized that the index is located on the image of the anterior segment, a control signal indicating a change amount in an optical axis direction of the imaging unit of a focal position of the image of the anterior segment relative to the imaging unit, wherein a position of the index is changeable by the operation unit.

16. A non-transitory computer-readable storage medium storing a program that causes a computer to execute the steps of the control method according to claim 15.

17. A control apparatus comprising:

a display control unit configured to cause a display unit to display an image of an anterior segment of a subject's eye captured by an imaging unit;

a recognition unit configured to recognize whether an index indicating a portion on the display unit is located on the image of the anterior segment; and a control unit configured to output, based on an operation signal output from an operation unit according to an operation on the operation unit when the recognition unit recognizes that the index is located on the image of the anterior segment, a control signal indicating a change amount in a distance between the anterior segment and an objective lens of the imaging unit in an optical axis direction of the imaging unit, wherein a position of the index is changeable by the operation unit.

18. The control apparatus according to claim 17, wherein the operation unit includes a first operation portion and a second operation portion, and wherein when the recognition unit recognizes that an index indicating an arbitrary position on the display unit is located on the image of the anterior segment, the control unit is configured to output, based on an operation signal output from the operation unit according to an operation on the first operation portion, a control signal indicating a change amount of a distance between the anterior segment and an objective lens of the imaging unit in an optical axis direction of the imaging unit, and to output, based on an operation signal output from the operation unit according to an operation on the second operation portion, a control signal indicating a change amount on a plane perpendicular to the optical axis direction of the imaging unit.

19. The control apparatus according to claim 18, wherein the operation unit is a mouse, the first operation portion is a wheel, and the second operation portion is a button.

20. An ophthalmologic apparatus comprising:

an imaging unit configured to capture an image of an anterior segment of a subject's eye;

a recognition unit configured to recognize whether an index indicating a portion on a display unit is located on the image of the anterior segment displayed on the display unit; and a changing unit configured to change a distance between the anterior segment and an objective lens of the imaging unit in an optical axis direction of the imaging unit based on a control signal output from a control unit according to an operation on an operation unit when the recognition unit recognizes that the index is located on the image of the anterior segment displayed on the display unit, wherein a position of the index is changeable by the operation unit.

21. The ophthalmologic apparatus according to claim 20, wherein the operation unit includes a first operation portion and a second operation portion, and wherein when the recognition unit recognizes that an index indicating an arbitrary position on the display unit is located on the image of the anterior segment, the control unit is configured to output, based on an operation signal output from the operation unit according to an operation on the first operation portion, a control signal indicating a change amount of a distance between the anterior segment and an objective lens of the imaging unit in an optical axis direction of the imaging unit, and to output, based on an operation signal output from the operation unit according to an operation on the second operation portion, a control signal indicating a change amount on a plane perpendicular to the optical axis direction of the imaging unit.

22. The ophthalmologic apparatus according to claim 21, wherein the operation unit is a mouse, the first operation portion is a wheel, and the second operation portion is a button.

23. A control method comprising:

causing a display unit to display an image of an anterior segment of a subject's eye captured by an imaging unit;

recognizing whether an index indicating a portion on the display unit is located on the image of the anterior segment; and outputting, based on an operation signal output from an operation unit according to an operation on the operation unit when the index is recognized as being located on the image of the anterior segment, a control signal indicating a change amount in a distance between the anterior segment and an objective lens of the imaging unit in an optical axis direction of the imaging unit, wherein a position of the index is changeable by the operation unit.

24. An ophthalmologic method comprising:
capturing an image of an anterior segment of a subject's eye;
recognizing whether an index indicating a portion on a display unit is located on the image of the anterior segment displayed on the display unit; and
changing a distance between the anterior segment and an objective lens of the imaging unit in an optical axis direction of the imaging unit based on a control signal output from a control unit according to an operation on an operation unit when the index is recognized as being located on the image of the anterior segment displayed on the display unit,
wherein a position of the index is changeable by the operation unit.

25. A non-transitory computer-readable storage medium storing a program that causes a computer to execute the steps of a control method comprising:
causing a display unit to display an image of an anterior segment of a subject's eye captured by an imaging unit;
recognizing whether an index indicating a portion on the display unit is located on the image of the anterior segment; and
outputting, based on an operation signal output from an operation unit according to an operation on the operation unit when the index is recognized as being located on the image of the anterior segment, a control signal indicating a change amount in a distance between the anterior segment and an objective lens of the imaging unit in an optical axis direction of the imaging unit,
wherein a position of the index is changeable by the operation unit.

26. A non-transitory computer-readable storage medium storing a program that causes a computer to execute the steps of an ophthalmologic method comprising:
capturing an image of an anterior segment of a subject's eye;
recognizing whether an index indicating a portion on a display unit is located on the image of the anterior segment displayed on the display unit; and
changing a distance between the anterior segment and an objective lens of the imaging unit in an optical axis direction of the imaging unit based on a control signal output from a control unit according to an operation on an operation unit when the index is recognized as being located on the image of the anterior segment displayed on the display unit,
wherein a position of the index is changeable by the operation unit.

\* \* \* \* \*